(12) United States Patent
O'Connell et al.

(10) Patent No.: US 10,238,375 B2
(45) Date of Patent: Mar. 26, 2019

(54) SURGICAL RETRACTOR

(71) Applicant: NuVasive, Inc., San Diego, CA (US)

(72) Inventors: Casey O'Connell, San Diego, CA (US); Joel Kohn, San Diego, CA (US); James Coleman Lee, San Diego, CA (US); David Banks, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/653,547

(22) Filed: Jul. 19, 2017

(65) Prior Publication Data

US 2019/0021715 A1    Jan. 24, 2019

(51) Int. Cl.
| | |
|---|---|
| *A61B 1/32* | (2006.01) |
| *A61B 17/02* | (2006.01) |
| *A61B 17/70* | (2006.01) |
| *A61B 17/16* | (2006.01) |
| *A61B 90/50* | (2016.01) |
| *A61B 17/00* | (2006.01) |
| *A61B 17/34* | (2006.01) |

(52) U.S. Cl.
CPC .............. *A61B 17/025* (2013.01); *A61B 1/32* (2013.01); *A61B 17/0206* (2013.01); *A61B 17/1671* (2013.01); *A61B 17/3423* (2013.01); *A61B 17/7074* (2013.01); *A61B 90/50* (2016.02); *A61B 2017/0046* (2013.01); *A61B 2017/00477* (2013.01)

(58) Field of Classification Search
CPC .................................................... A61B 17/025
See application file for complete search history.

(56) References Cited

U.S. PATENT DOCUMENTS

| | | | |
|---|---|---|---|
| 2,623,517 | A | 12/1952 | Barlow et al. |
| 3,168,093 | A | 2/1965 | Gauthier |
| 3,221,743 | A | 12/1965 | Thompson |
| 3,724,449 | A | 4/1973 | Gauthier |
| 3,749,088 | A | 7/1973 | Kohlmann |
| 3,965,890 | A | 6/1976 | Gauthier |
| 4,010,741 | A | 3/1977 | Gauthier |
| 4,099,521 | A | 7/1978 | Nestor et al. |

(Continued)

FOREIGN PATENT DOCUMENTS

WO    WO2015054070    4/2015

OTHER PUBLICATIONS

International Search Report dated Aug. 17, 2017 for International Application No. PCT/US2017/017700, 5 pages.

(Continued)

*Primary Examiner* — Eduardo C Robert
*Assistant Examiner* — Tara R Carter
(74) *Attorney, Agent, or Firm* — NuVasive, Inc.

(57) ABSTRACT

A surgical retractor assembly is provided having a frame that releasably couples two retractor blades. The retractor blades are coupled to the frame via a pair of mobile carriages that engage a track on the frame. A third retractor blade is configured to be independent of the frame with the first two retractor blades. The independent blade may be fixably positionable in the patient by a direct coupling to a rigid table mount. The retractor assembly may be utilized for creating anterior access to spinal target site while the patient is oriented in the lateral decubitus position.

25 Claims, 21 Drawing Sheets

(56) References Cited

U.S. PATENT DOCUMENTS

| | | |
|---|---|---|
| 4,254,763 A | 3/1981 | McCready et al. |
| 4,434,791 A | 3/1984 | Darnell |
| 4,457,300 A | 7/1984 | Budde |
| 4,510,926 A | 4/1985 | Inaba |
| 4,617,916 A | 10/1986 | LeVahn et al. |
| 4,971,038 A | 11/1990 | Farley |
| 5,025,780 A | 6/1991 | Farley |
| 5,242,240 A | 9/1993 | Gorham |
| 5,400,772 A | 3/1995 | LeVahn et al. |
| 5,529,358 A | 6/1996 | Dinkier et al. |
| 5,616,117 A | 4/1997 | Dinkier et al. |
| 5,792,046 A | 8/1998 | Dobrovolny |
| 5,897,087 A | 4/1999 | Farley |
| 5,899,627 A | 5/1999 | Dobrovolny |
| 5,902,233 A | 5/1999 | Farley et al. |
| 5,951,467 A | 9/1999 | Picha et al. |
| 5,967,973 A | 10/1999 | Sherts et al. |
| 5,984,865 A | 11/1999 | Farley et al. |
| 6,017,008 A | 1/2000 | Farley |
| 6,033,363 A | 3/2000 | Farley et al. |
| 6,083,154 A | 7/2000 | Liu et al. |
| 6,102,854 A | 8/2000 | Cartier et al. |
| 6,190,312 B1 | 2/2001 | Fowler, Jr. |
| 6,213,940 B1 | 4/2001 | Sherts et al. |
| 6,254,532 B1 * | 7/2001 | Paolitto ............... A61B 17/0206 600/201 |
| 6,264,396 B1 | 7/2001 | Dobrovolny |
| 6,273,853 B1 | 8/2001 | Cartier et al. |
| 6,296,609 B1 | 10/2001 | Brau |
| 6,416,465 B2 | 7/2002 | Brau |
| 6,537,212 B2 | 3/2003 | Sherts et al. |
| 6,602,190 B2 | 8/2003 | Dobrovolny |
| 6,648,818 B2 | 11/2003 | Cartier et al. |
| 6,733,445 B2 | 5/2004 | Sherts et al. |
| 6,763,775 B1 | 7/2004 | Sweeting |
| 6,764,444 B2 | 7/2004 | Wu et al. |
| 7,014,609 B2 | 3/2006 | Cartier et al. |
| 7,052,457 B2 * | 5/2006 | Fanous ............... A61B 17/0293 600/220 |
| 7,156,805 B2 | 1/2007 | Thalgott et al. |
| 7,232,411 B2 | 6/2007 | Dinkier, II et al. |
| 7,338,442 B2 | 3/2008 | Mulac et al. |
| 7,435,219 B2 | 10/2008 | Kim |
| 7,556,600 B2 | 7/2009 | Landry et al. |
| 7,665,939 B1 | 2/2010 | Cardona |
| 7,749,163 B2 | 7/2010 | Mulac et al. |
| 7,811,230 B2 | 10/2010 | Hsueh et al. |
| 8,100,827 B2 | 1/2012 | Farley |
| 8,100,828 B2 | 1/2012 | Frey et al. |
| 8,231,528 B1 | 7/2012 | Friedrich et al. |
| 8,617,064 B2 | 12/2013 | Farley |
| 8,894,029 B2 | 11/2014 | Agbodoe et al. |
| 8,911,364 B2 * | 12/2014 | Feigenwinter ...... A61B 17/0293 600/201 |
| 8,932,215 B2 | 1/2015 | Friedrich et al. |
| 9,216,125 B2 * | 12/2015 | Sklar ................... A61G 13/121 |
| 9,283,091 B2 | 3/2016 | Melkent et al. |
| 9,320,506 B2 | 4/2016 | Bertagnoli et al. |
| 9,427,328 B2 | 8/2016 | Drochner et al. |
| 9,433,406 B2 | 9/2016 | Slagle et al. |
| 9,549,723 B2 | 1/2017 | Hynes et al. |
| 9,615,733 B2 | 4/2017 | Nottmeier |
| 2005/0171405 A1 | 8/2005 | Rowland et al. |
| 2006/0149138 A1 | 7/2006 | Fanous |
| 2006/0224044 A1 | 10/2006 | Marchek et al. |
| 2007/0038033 A1 | 2/2007 | Jones et al. |
| 2007/0161867 A1 | 7/2007 | Fowler et al. |
| 2007/0235038 A1 | 10/2007 | Alinsod et al. |
| 2007/0238933 A1 | 10/2007 | Alinsod et al. |
| 2009/0018401 A1 | 1/2009 | Kim |
| 2010/0274094 A1 | 10/2010 | Abdelgany et al. |
| 2015/0100129 A1 | 4/2015 | Waugh et al. |
| 2015/0265320 A1 | 9/2015 | Hynes et al. |
| 2016/0008140 A1 | 1/2016 | Melkent et al. |
| 2016/0081681 A1 | 3/2016 | Waugh et al. |
| 2016/0081818 A1 | 3/2016 | Waugh et al. |
| 2016/0089129 A1 | 3/2016 | Hennard et al. |
| 2016/0095627 A1 | 4/2016 | Michelle |
| 2016/0106553 A1 | 4/2016 | Melkent et al. |
| 2016/0213489 A1 | 7/2016 | Drochner et al. |
| 2016/0273676 A1 | 9/2016 | Beale et al. |
| 2017/0007227 A1 | 1/2017 | Hynes et al. |

OTHER PUBLICATIONS

Written Opinion of the International Searching Authority dated Aug. 17, 2017 for International Application No. PCT/US2017/017700, 12 pages.

* cited by examiner

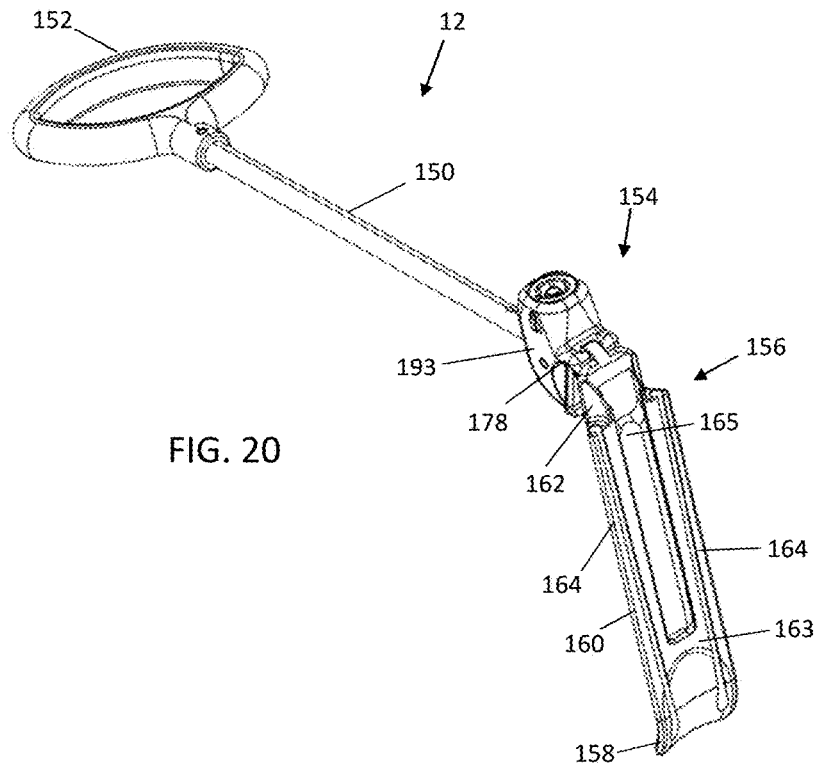
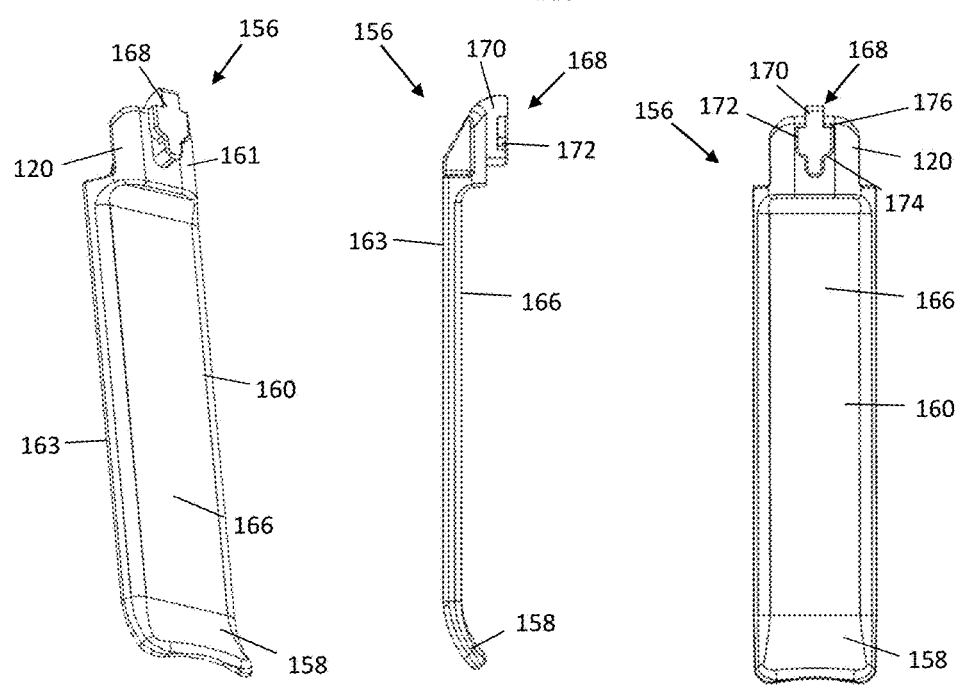
FIG. 20   FIG. 21   FIG. 22   FIG. 23

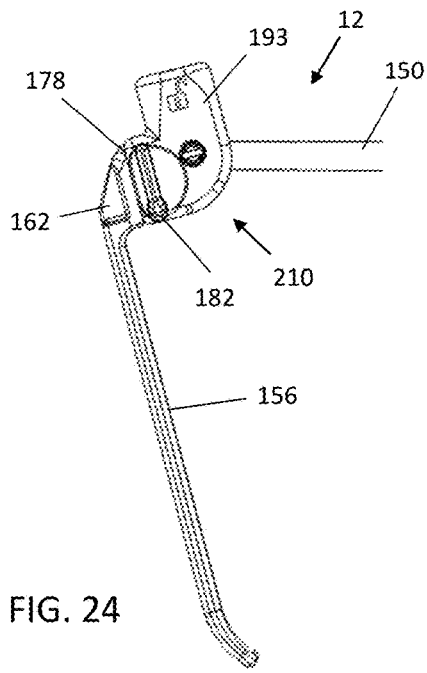
FIG. 24
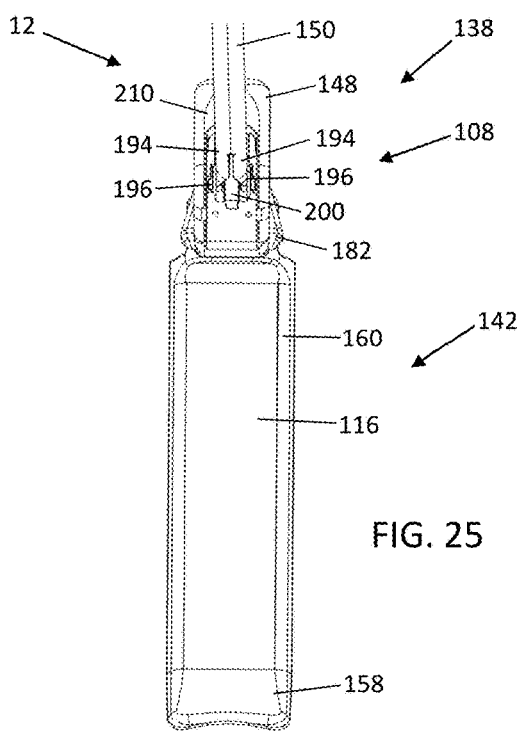
FIG. 25
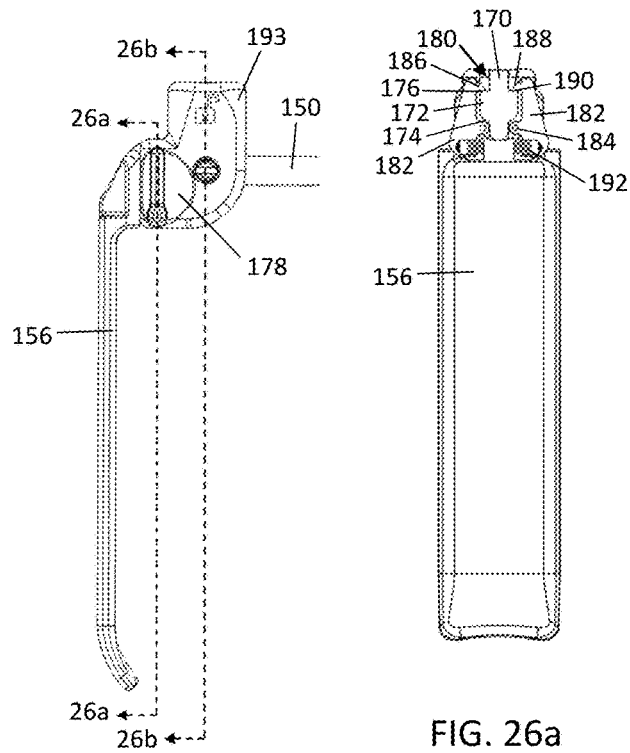
FIG. 26
FIG. 26a
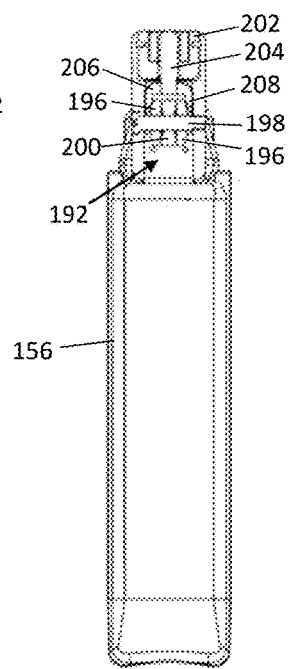
FIG. 26b

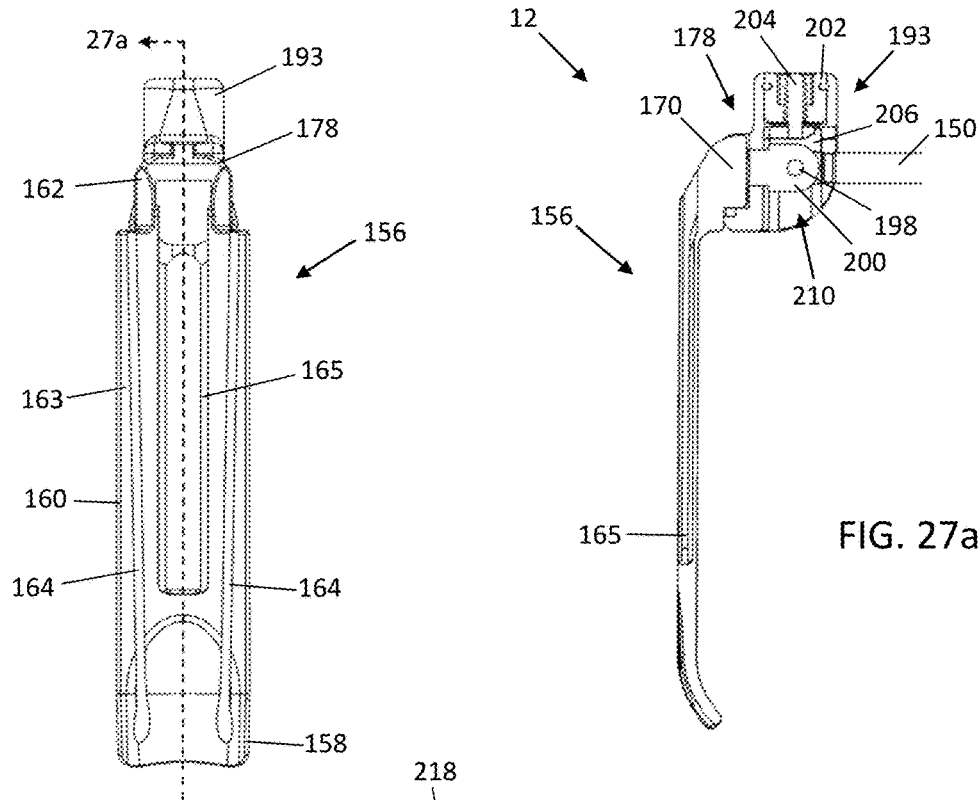
FIG. 27
FIG. 27a
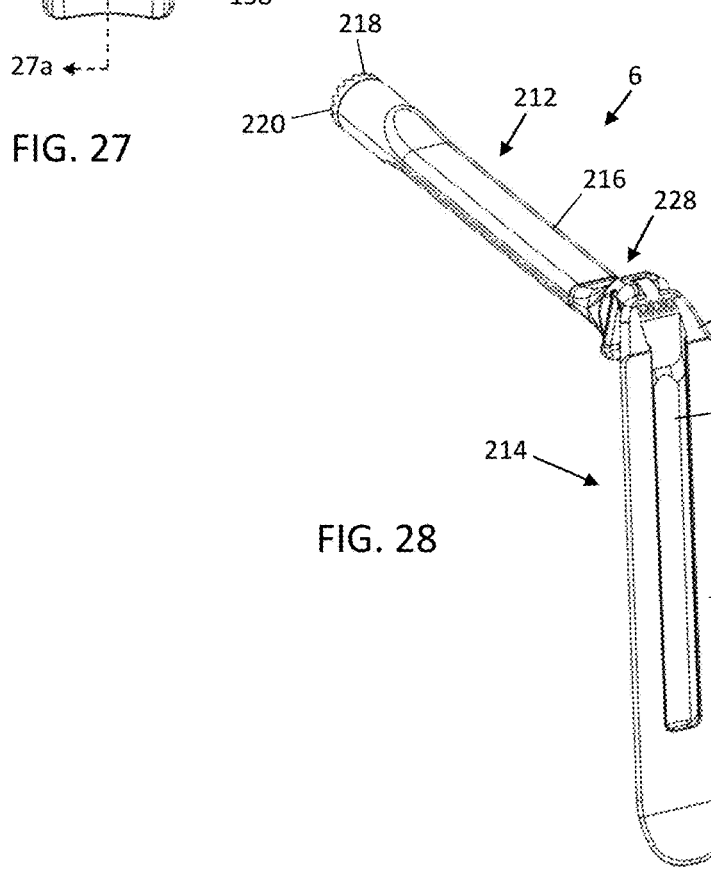
FIG. 28

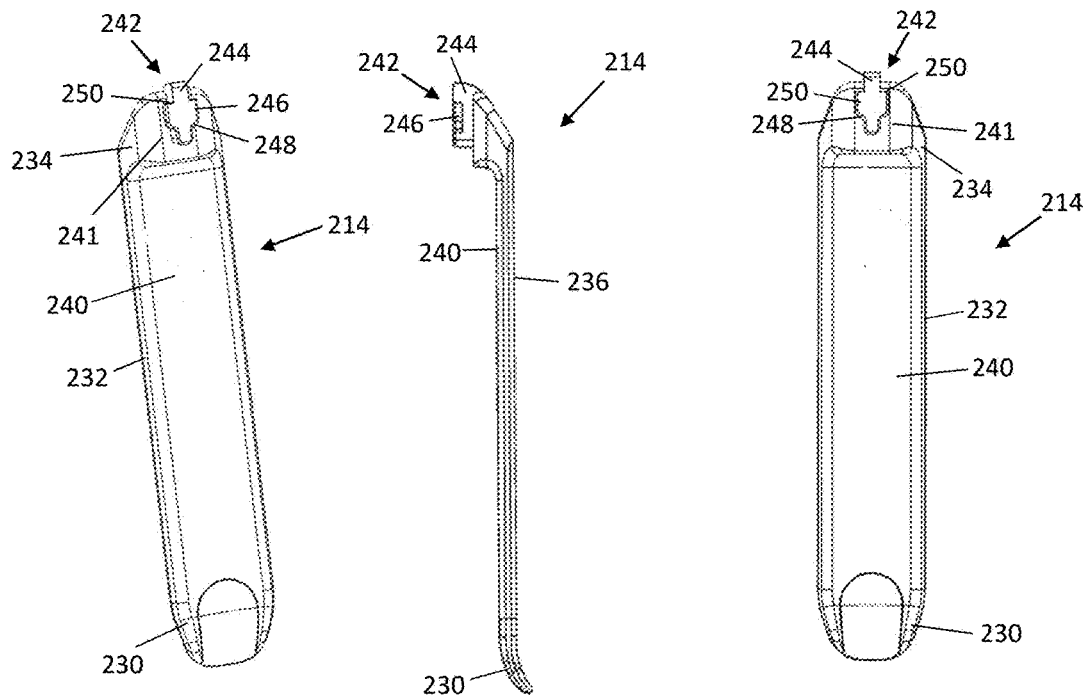
FIG. 29　　FIG. 30　　FIG. 31
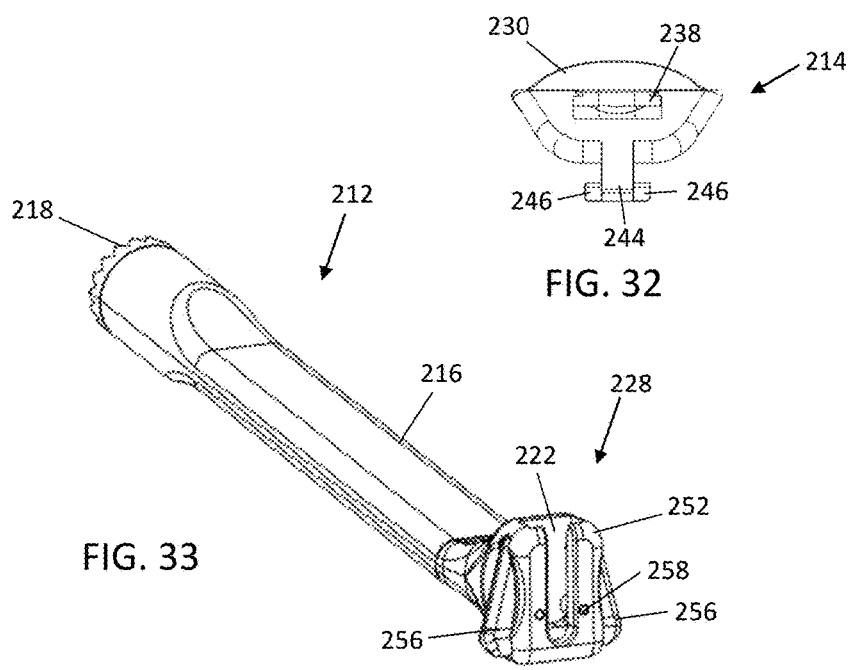
FIG. 32
FIG. 33

SURGICAL RETRACTOR

FIELD

The present disclosure relates to surgical access instruments and methods for using them to perform surgical procedures on the spine.

BACKGROUND

The spine is critical in human physiology for mobility, support, and balance. The spine protects the nerves of the spinal cord, which convey commands from the brain to the rest of the body, and convey sensory information from the nerves below the neck to the brain. Even minor spinal injuries can be debilitating to the patient, and major spinal injuries can be catastrophic. The loss of the ability to bear weight or permit flexibility can immobilize the patient. Even in less severe cases, small irregularities in the spine can put pressure on the nerves connected to the spinal cord, causing devastating pain and loss of coordination.

Fusion is one method for treating the symptoms that can accompany a damaged spinal disc, or other spinal pathologies that can result in the impingement of neural structures. The primary goals of fusion procedures are generally to reposition (e.g. increase space and/or alignment between vertebrae) portions of the spine, decompressing impinged neural structures in the process, and to provide stability to maintaining the position of those vertebrae. Most commonly, a fusion procedure is performed by removing some or all of the disc material between the vertebral segments to be fused and depositing one or more interbody spacers into the disc space. Over time new bone grows across the disc space to provide a solid bridge between the vertebrae. As an alternative to fusion, other motion preserving implants can also be implanted in the disc space to reposition the vertebrae while still maintaining the ability of the vertebrae to move relative to each other.

In all of these procedures the ability to safely access the targeted portions of the spine and to effectively manipulate the instrumentation used to affect the work done on the spine is crucial to the success of the procedure. Traditionally, lumbar interbody fusion has been performed through procedures accessing the spine from the anterior (anterior lumbar interbody fusion (ALIF)) or posterior, (posterior lumbar interbody fusion (PLIF) and transforaminal lumbar interbody fusion (PLIF)) aspect of the patient. These procedures each present their own advantages and disadvantages. Posterior-access procedures, for example, involve traversing a shorter distance within the patient to establish the operative corridor and can be augmented with posterior fixation without requiring the patient to be flipped during the surgery, albeit at the price of stripping away or cutting back muscles, and having to reduce or cut away part of the posterior bony structures (i.e. lamina, facets, spinous process) in order to reach the target site, and presenting a relatively small access window within which to operate and advance an implant through. On the other hand anterior-access procedures do not involve stripping or cutting back muscles, or reducing or cutting away bony structures to reach the surgical target site, and also present a large access window, allowing for easier tool manipulation and the implantation of a larger, more stable interbody implant. However, they also require traversing through a much greater distance within the patient and mobilizing the abdominal contents, and sometimes the vascular structures running along the front of the spine, to establish the operative corridor.

In the last decade, advances in technology and technique have also made a lateral approach to the spine a popular alternative to anterior and posterior approaches. The lateral approach achieves many of the advantages of both the posterior and anterior approaches (e.g. avoids stripping or cutting of back muscles, abdominal contents, and vascular structures while presenting a large exposure through which a large implant can be advanced. On disadvantage with the lateral approach however is that the L5-S1 disc space, and sometimes the L4-L5 disc space cannot not be accessed due to the presence of the iliac crest. Thus, in many cases where multiple levels, including L5-S1 and/or L4-L5, are to be fused, the surgeon must choose between using the lateral approach on the upper level(s) and then flipping the patient in the middle of the surgery to perform an ALIF on the lower level(s), or foregoing the advantages that can accompany the lateral approach and doing each level through an anterior approach in order to avoid flipping the patient. The instruments and methods described herein are directed towards providing additional flexibility and options to the surgeon to eliminate, or at least reduce, these and other challenges.

SUMMARY

The present disclosure describes a retractor assembly useful for forming an operative corridor to a target site at the spine of a patient. The retractor assembly may be particularly useful in forming an operative corridor to the lumbar spine from an anterior approach with the patient lying in the lateral decubitus position, for example, a Lateral ALIF.

The retractor assembly includes a main retractor and offset or independent retractor set apart from the main retractor. The main retractor has a frame, a first blade assembly, second blade assembly, and a pair of carriages that couple the blade assemblies to the frame. The offset retractor includes a third blade assembly. The frame extends along an arc between a pair of ends. In one example frame arc extends approximately 150° such that the frame has a crescent shape. In the same example, the diameter of the arc is approximately 9". This configuration with the frame extending less than halfway around the circle and the independent third blade is designed to maximize the amount of unencumbered perimeter surrounding the operative corridor, thus minimizing the interference with the surgeon's use of tools through the corridor and imaging.

A track runs along the frame and receives carriages that hold the retractor blade assemblies. The carriage adjustably couples the first and second blade assemblies to the frame. The carriage has an unlocked configuration in which the carriage can translate along the track and the orientation of the associated blade assembly can be adjusted relative to the frame with 5° of freedom. The carriage also has a locked configuration in which adjustment of the carriage position and blade orientation is inhibited.

The first blade assembly includes a blade post that couples to the carriage and a fixed angle retractor blade. The first retractor blade may be a narrow blade and may be 18 mm wide according to one example. The first blade may include an anchor channel through which an anchor may be directed into the vertebral bone to fix the distal end of the blade relative to the bone. The second blade assembly includes a blade post that couples to the carriage and an adjustable angle retractor blade. The second retractor blade may be a wide retractor blade, and may be 25 mm wide according to one example. A pair of anchor channels pass through the second blade through which anchors may be directed into the vertebral bone to fix the distal end of the blade relative to the bone. The second blade has an adjustment mechanism such that the angle of the blade relative to the post can be adjusted to add additional flexibility to the overall positioning of the retractor assembly. While the first blade is shown as a fixed and narrow blade and the second blade assembly is shown as an adjustable and wide blade, it should be appreciated that the either or both of the first and second blades may be fixed or adjustable and wide or narrow. The third blade assembly includes a blade extension and third blade. The blade extension connects to a rigid mount to secure the position of the third retractor blade without the need for attaching the third blade to a frame. The third blade is shown as a wide blade and may be approximately 25 mm wide according to one example. The third blade may alternatively be a narrow blade. The third blade may include a forward facing distal curve to engage against the side of the vertebral body.

In use, the retractor assembly is deployed to create and maintain an access or operative corridor to the spine of a patient. One example technique for performing a Lateral ALIF procedure to the L5-S1 disc space with the retractor assembly positioning the patient on the table in the lateral decubitus position. An oblique incision is made lateral to the rectus and cephalad to the inguinal ligament and an alternating blunt scissor and finger dissection is used to enter the retroperitoneal space create a space through which the retractor blades may pass. The second (lateral) blade is advanced through the retroperitoneal space and positioned medial to the descending common iliac vessels and lateral to the L5-S1 disc space with the distal end docked on the disc. The distal end of the blade may be anchored with a bone anchor through one of the anchor channels and into the S1 vertebral body. Next, the first (cranial) retractor blade may be guided down to the superior aspect of the disc space and below the descending vessel bifurcation. The distal end of the blade may be anchored with the placement of a bone anchor through the anchor channel into the L5 body. The frame may then be assembled with a pair of carriages loaded into the track. The frame is then centered around the incision and a rigid table mount, for example, an A-arm mount may then be coupled to the frame. The first and second retractor assemblies are then coupled to the frame by engaging them with their respective carriages. The position and orientation of the carriage/blade may be adjusted in any of the 5° of freedom in order to engage the post with the carriage. Once the blades are coupled, the carriages may be manipulated to their locked configuration. With the main retractor in place, the offset or independent retractor is placed in the medial position. The third (medial) blade may be advanced through the incision and positioned over the L5-S1 disc space. The third blade assembly is then rigidly fixed in position by attaching to a rigid table mount, by way of example, an A-arm table mount. Once access to the disc space is achieved has been achieved, the surgeon may proceed with disc space preparation and implant placement.

According to a first example, a retractor assembly is described forming an operative corridor to a spinal target site. The retractor assembly includes a main retractor assembly having a frame, a first mobile carriage coupled to the frame and a first retractor blade assembly coupled to the first mobile carriage. The main retractor also includes a second mobile carriage coupled to the frame and a second retractor blade assembly coupled to the second mobile carriage. An independent retractor assembly having a third retractor blade assembly that is directly coupleable to a rigid mount is also included.

According to another aspect of the first example, the frame includes track and the first mobile carriage and the second mobile carriage translate along the track.

According to another aspect of the first example, the track includes a lower groove and an upper neck narrower than the lower groove.

According to another aspect of the first example, the first and second mobile carriages each include a foot dimensioned to slide along the lower groove underneath the upper neck.

According to another aspect of the first example, the frame is arcuate and the track is arcuate extending from a first end to a second end along the arcuate frame.

According to another aspect of the first example, the arcuate frame extends along an arc length of 150°.

According to another aspect of the first example, the arc radius is 9 inches.

According to another aspect of the first example, the track includes an opening lacking the upper neck and the first and second carriage foots are inserted into the lower groove.

According to another aspect of the first example, the frame is made of carbon fiber.

According to another aspect of the first example, the frame includes a connector site that is coupleable to a rigid mount.

According to another aspect of the first example, the first mobile carriage and the second mobile carriage each have a locked configuration in which translation along the track is inhibited.

According to another aspect of the first example, each of the first mobile carriage and second mobile carriage include an unlocked configuration in which the coupled blade assembly is adjustable with five degrees of freedom.

According to another aspect of the first example, the first and second carriages each include a column extending upwards from the foot and a bearing seat, blade holder, compression cap, and locking cap stacked atop one another along the column.

According to another aspect of the first example, the bearing seat has a spherical bearing surface and the blade holder has a spherical bearing socket that bears on the spherical bearing surface.

According to another aspect of the first example, the upper surface of the blade holder is a spherical surface and the compression cap has a spherical under surface that bears on the upper surface of the blade holder.

According to another aspect of the first example, the blade holder rotates about the spherical bearing surface of the bearing seat and the rotational freedom of the blade holder defines an elliptic cone.

According to another aspect of the first example, the blade holder includes a blade channel that receives a blade post of the first or second blade assembly.

According to another aspect of the first example, one of the first and second blade assemblies is a fixed assembly wherein the angle of the retractor blade is fixed relative to the blade post.

According to another aspect of the first example, one of the first and second blade assemblies is an adjustable assembly wherein the angle of the retractor blade relative to the blade post is adjustable.

According to a second example, a system for creating an anterior access corridor to a lumber spine with the patient in the lateral decubitus position is provided. The system includes a three bladed retractor assembly. Two of the three retractor blades of the three bladed retractor assembly are coupled to an arcuate frame having an arc length of 180° or less. The third retractor blade is independent from the arcuate frame and is directly coupled to a rigid table mount to hold the retractor blade in position.

According to another aspect of the second example, the two retractor blades coupled to the arcuate frame are each coupled to the frame by a carriage.

According to another aspect of the second example, each carriage includes an unlocked position in which the associated retractor blade is adjustable with five degrees of freedom relative to the frame.

According to another aspect of the second example, the carriages are movable along a track of the frame in the unlocked position.

According to another aspect of the second example, each carriage includes a locked position in which movement along the track is arrested.

According to another aspect of the second example, the locked position inhibits all movement of the associated retractor blade relative to the frame.

BRIEF DESCRIPTION OF THE DRAWINGS

FIG. 20 is perspective view of a second retractor blade assembly forming part of the retractor assembly of FIG. 1;
FIG. 21 is a rear perspective view of a retractor blade of the second retractor blade assembly of FIG. 20;
FIG. 22 is a side view of the retractor blade of FIG. 21;
FIG. 23 is a rear view of the retractor blade of FIG. 21;
FIG. 24 is a side view of a distal end of the second retractor blade assembly of FIG. 20 with the blade connector and attached blade angulated relative to a blade post;
FIG. 25 is a rear view of the distal end of the of the second retractor blade assembly of FIG. 20;
FIG. 26 is a side view of the distal end of the second retractor blade assembly of FIG. 20;
FIG. 26a is a cross-section view of the distal end of the second retractor blade assembly of FIG. 26;
FIG. 26b is another cross-section view of the distal end of the second retractor blade assembly of FIG. 26;
FIG. 27 is a front view of the distal end of the second retractor blade assembly of FIG. 20;
FIG. 27a is a cross-section view of the distal end of the second retractor blade assembly of FIG. 27;
FIG. 28 is a perspective view of a third retractor blade assembly forming part of the retractor assembly of FIG. 1;
FIG. 29 is a rear perspective view of the retractor blade of FIG. 28;
FIG. 30 is a side view of the retractor blade of FIG. 28;
FIG. 31 is a rear view of the retractor blade of FIG. 28;
FIG. 32 is a top view of the retractor blade of FIG. 28;
FIG. 33 is a perspective view of a blade extension forming part of the third blade assembly of FIG. 28.

DETAILED DESCRIPTION

Illustrative embodiments of a surgical retractor assembly are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The retractor assembly and methods of using the retractor assembly disclosed herein boasts a variety of inventive features and components that warrant patent protection, both individually and in combination.

Figure 1:
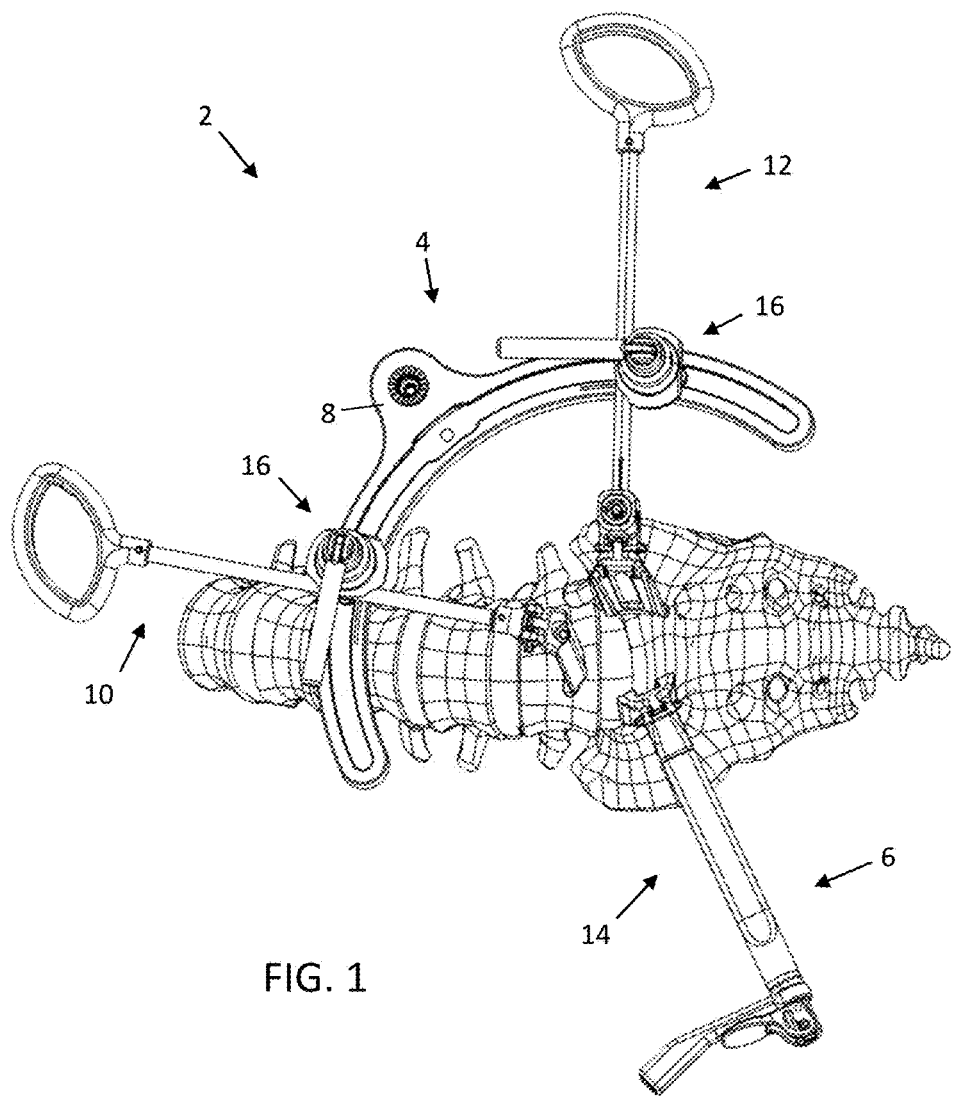
FIG. 1 is a perspective view of a retractor assembly configured for use in an anterior access surgery with the patient in the lateral decubitus position, according to one example embodiment.
Figure 2:
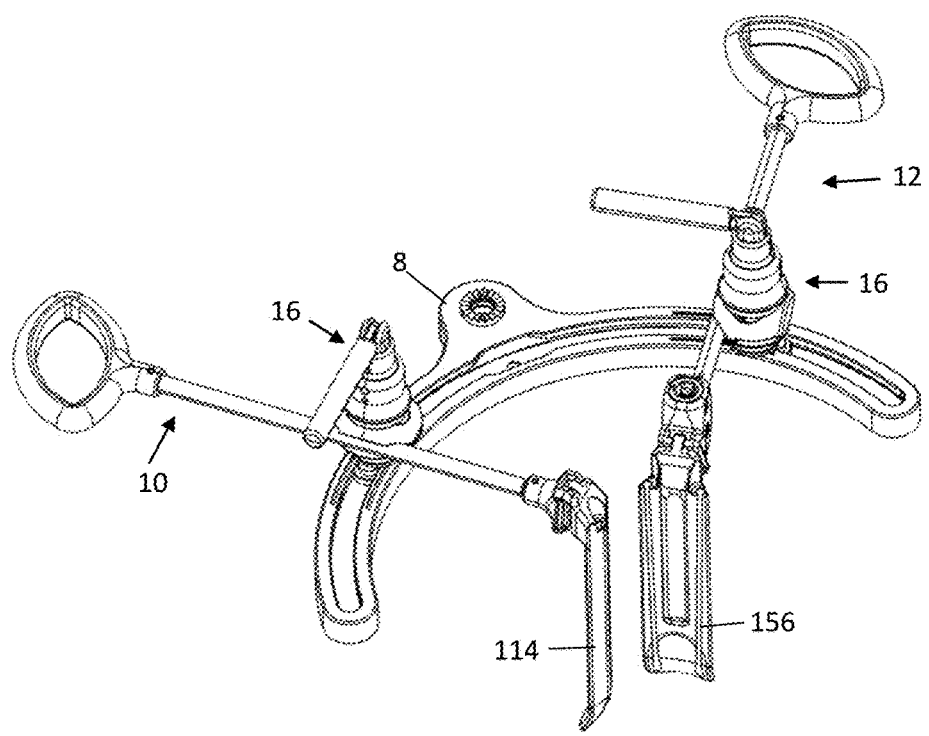
FIG. 2 is a perspective view of a main retractor assembly of the retractor assembly of FIG. 1.

An illustrative embodiment of a retractor assembly 2 is shown in FIG. 1. The retractor assembly 2 is depicted in configuration for performing an anterior approach to the spine with the patient lying in the lateral decubitus position. For expediency, this may be referred to herein as the Lateral ALIF approach or Lateral ALIF configuration, however, it should be appreciated that surgeries other than fusion (e.g. artificial disc replacement, corpectomy) may similarly be performed through the access corridor created. The approach shown in FIG. 1 is to the L5-S1 disc space. The retractor assembly 2 includes a main retractor 4 and offset retractor 6 set independent from the main retractor. The main retractor 4, shown in FIG. 2, has a frame 8, a first blade assembly 10, second blade assembly 12, and a pair of carriages 16 that couple the blade assemblies to the frame. The offset retractor 6 includes a third blade assembly 14. According to the example Lateral ALIF configuration shown, the first blade assembly may be positioned as the cranial blade, the second blade assembly as the lateral blade, and the third blade assembly as the midline blade.

Figure 3:
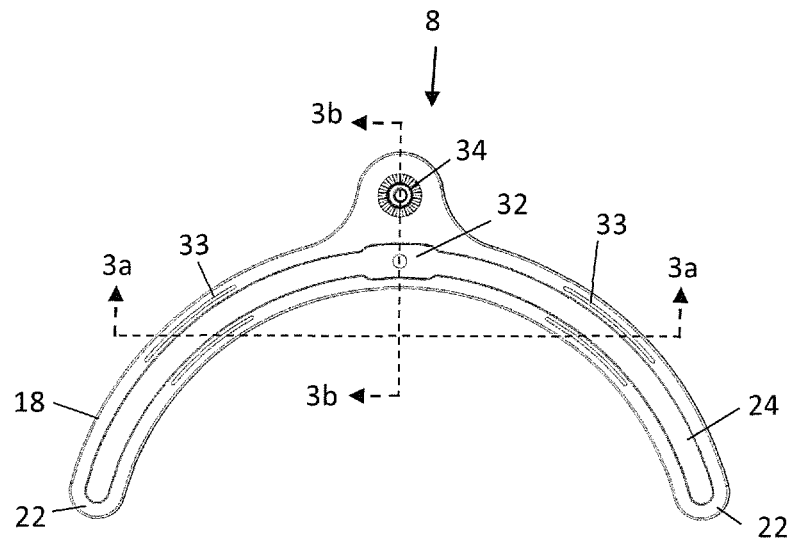
FIG. 3 is a top side view of a frame forming part of the retractor assembly of FIG. 1.

With reference to FIG. 3, the frame 8 has an upper surface 18, lower surface 20, and extends along an arc between a pair of ends 22. In the example embodiment shown the frame arc extends approximately 150° such that the frame has a crescent shape and a diameter of approximately 9". Together with the minimalist profile of the offset retractor 6, this crescent frame 8 provides flexibility to the surgeon while operating through the retractor (e.g. performing a discectomy or placing an implant) as it minimizes encumbrances on ability to freely manipulate the instruments used during the procedure. It is contemplated that the arc may in some embodiments depart from the arc of a circle, for example, the arc could also be the arc of an ellipse or an oval. It is further contemplated that the frame 8 may define an arc length of greater than 150° or less than 150° and a diameter of greater than 9" or less than 9". By way of example, the arc may extend from 90°-180° and the diameter may range between 6" and 12". According to a preferred example, the frame 8 may also be constructed of carbon fiber or other composite materials to minimize interference with flourovisibility.

Figure 3A:
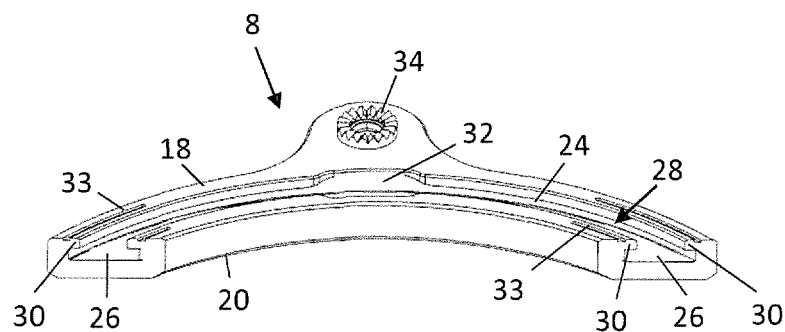
FIG. 3a is a perspective cross-section view of the frame of FIG. 3.
Figure 3B:
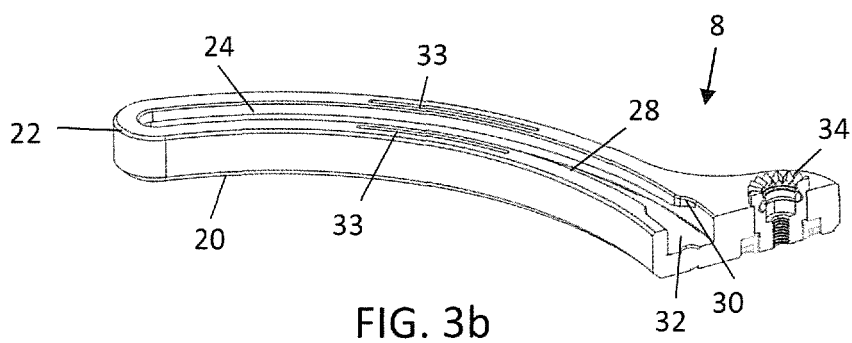
FIG. 3b is another perspective view of a cross-section of the frame of FIG. 3.
Figure 4:
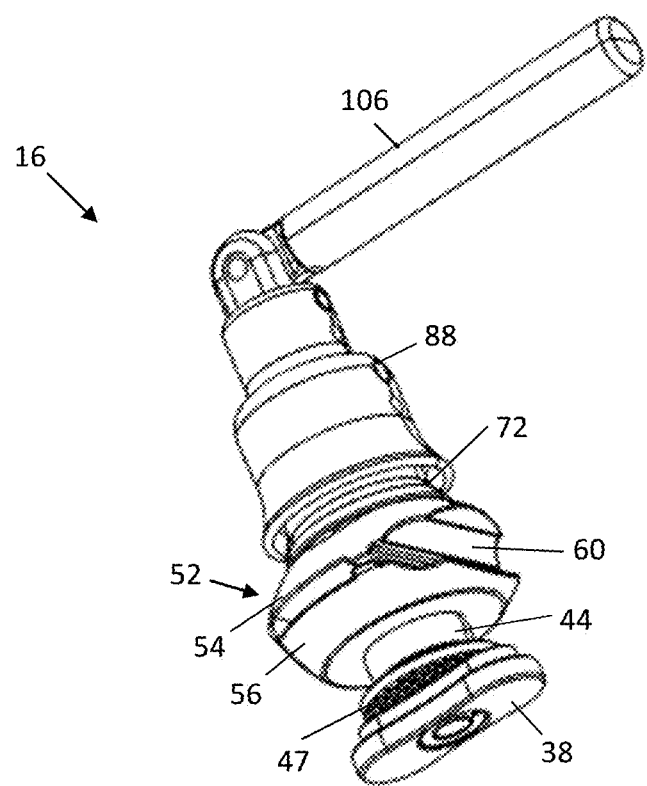
FIG. 4 is a perspective view of a carriage forming part of the retractor assembly of FIG. 1.
Figure 5:
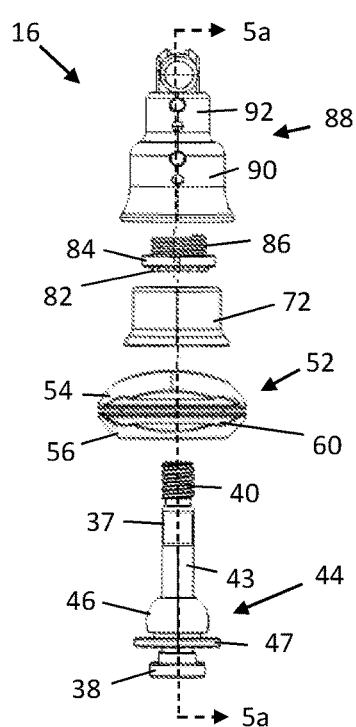
FIG. 5 is an exploded side view of the carriage of FIG. 4.
Figure 5A:
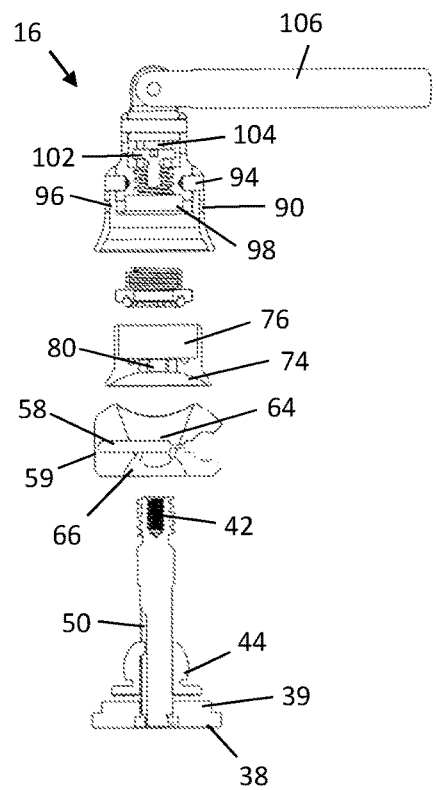
FIG. 5a is a cross-section view of the carriage of FIG. 5.
Figure 6A:
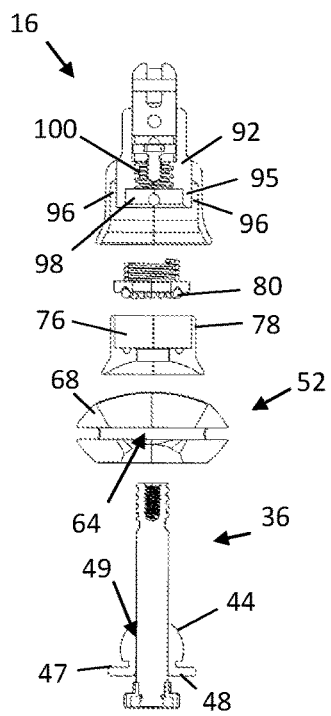
FIG. 6a is a cross-section view of the carriage of FIG. 6.
Figure 6:
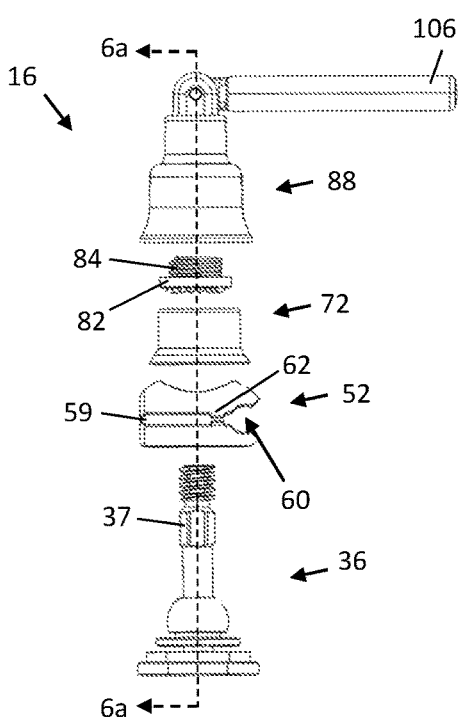
FIG. 6 is an exploded front view of the carriage of FIG. 4.
Figure 7:
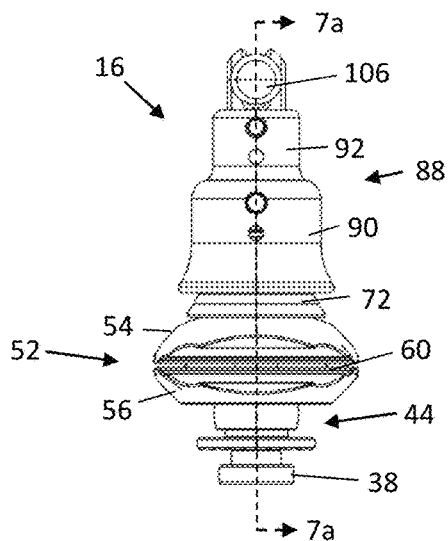
FIG. 7 is a side view of the carriage of FIG. 4 in an unlocked configuration.
Figure 7A:
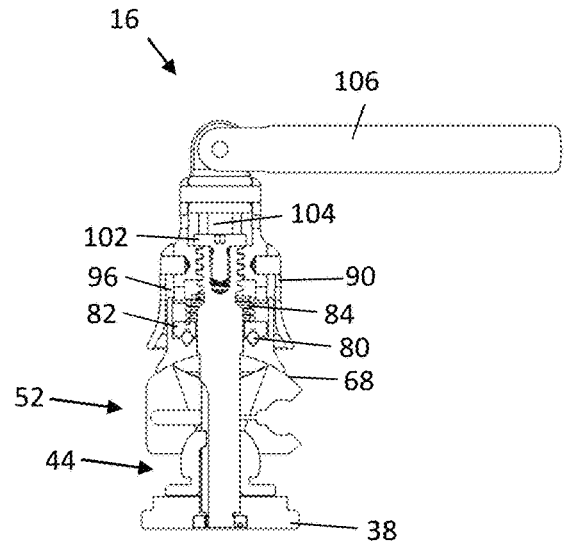
FIG. 7a is a cross-section view of the carriage of FIG. 7.
Figure 8A:
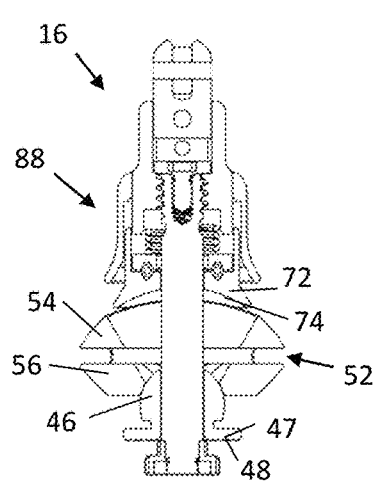
FIG. 8a is a cross-section view of the carriage of FIG. 8.
Figure 8:
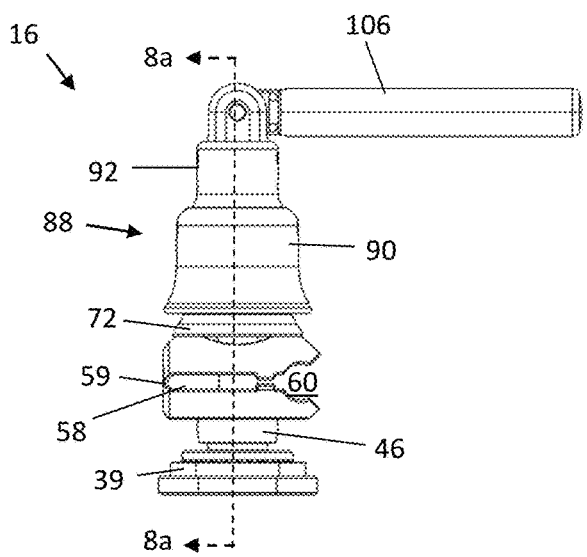
FIG. 8 is a front view of the carriage of FIG. 4 with the carriage in an unlocked configuration.
Figure 9:
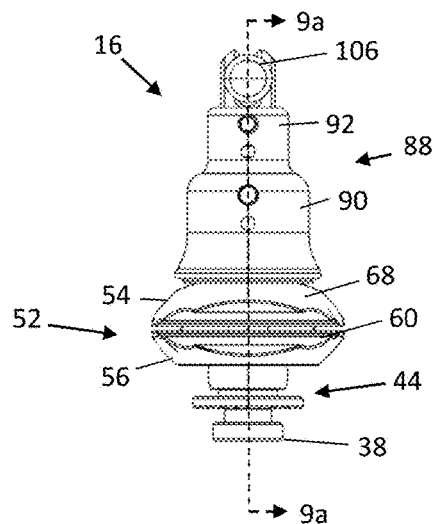
FIG. 9 is a side view of the carriage of FIG. 4 in a locked configuration.
Figure 9A:
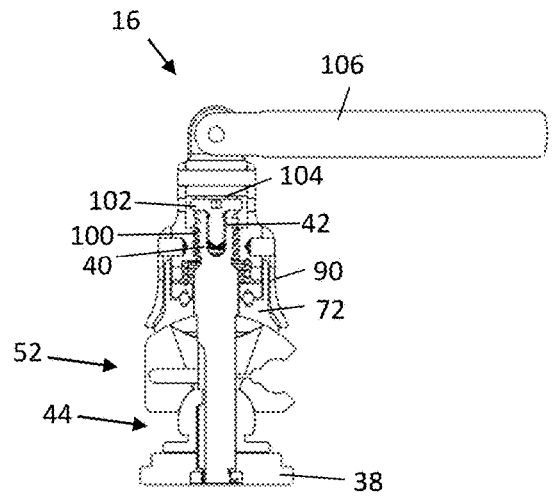
FIG. 9a is a cross-section view of the carriage of FIG. 9.
Figure 10A:
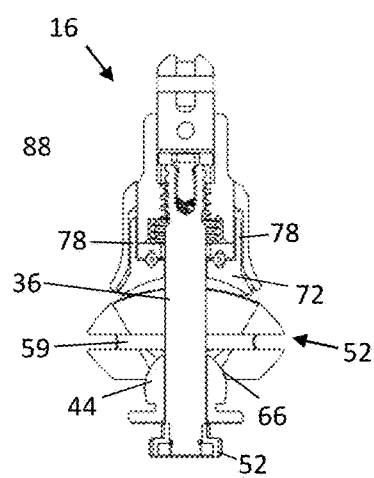
FIG. 10a is a cross-section view of the carriage of FIG. 10.
Figure 10:
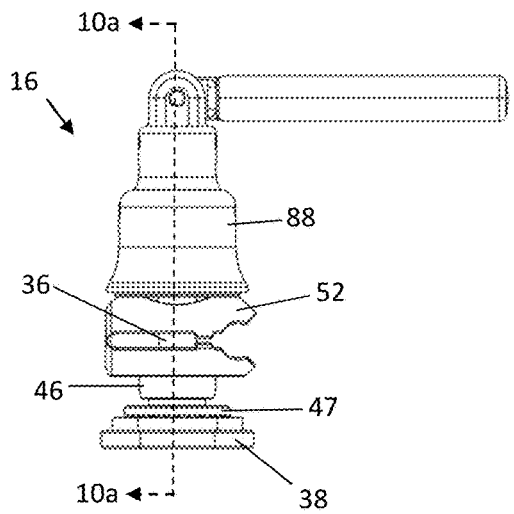
FIG. 10 is a front view of the carriage of FIG. 4 with the carriage in a locked configuration.

A track 24 runs along the frame between the pair of ends 22. The track 24 is open to the upper surface 18 and includes a distal groove 26 and a proximal neck 28 that is narrower than the distal groove. The proximal neck 28 is formed by a pair of ledges 30 that extend over the distal groove 26 as best viewed in FIG. 3a. An opening 32 is situated on the track 24 and is marked by the absence of ledges 30 such that the carriages 16 are top loaded onto the track through the opening 32. Carriage markers 33 may be included on the frame to help with initial set up of the retractor 4. That is, the markers 33 mark the general positions in which the carriages 16 will rest along the frame when utilized for a Lateral ALIF procedure. The carriages 16 may be pre-loaded to those positions such that only minimally adjustment is later needed in order to couple the first and second blade assemblies 10, 12. A connector 34 (e.g. the poker chip connector shown) is situated on the frame 8 and may be attached to a rigid mount (e.g. an A-arm table mount) to fix the position of the frame 8. Some alternate embodiments of the frame 8 may have more than one track 24 covering subsets of the distance between the ends 22. For example, shorter distinct tracks could be provided for to each receive an individual carriage.

An example embodiment of the carriage 16 is illustrated in FIGS. 6-10. The carriage 16 serves to adjustably couple the first and second blade assemblies 10, 12 to the frame 8. Carriage 16 has an unlocked configuration (FIGS. 7-8) in which the carriage can translate along the track 24 to adjust the position of the carriage on the frame 8 and the orientation of the blade assembly, 12, 14 can be adjusted relative to the frame. In the locked configuration (FIGS. 9-10) adjustment of the carriage position and blade orientation is prohibited. The embodiment of the carriage 16 shown allows the blade assembly 12, 14 to move with five degrees of freedom (translation in two dimensions as well as yaw, pitch, and roll rotational motion) relative to the frame 8. For the purposes of this discussion, yaw refers to rotation about the distal/proximal axis of the carriage; pitch refers to rotation about an axis parallel to a tangent to the frame 8 at the location of the carriage 16; and roll refers to rotation about an axis that intersects the frame 8 at the location of the carriage 16 and the center of the circle generally defined by the frame 8.

The foundation of the carriage 16 is a column 36. The column 36 includes a foot 38 at the distal end opposite a proximal head 40. A shaft 43 extends between the foot 38 and the head 40 and mounted on the shaft 43 is a bearing seat 44. The head 40 is threaded externally with a reverse thread and also includes an internal thread 42. Adjacent the head 44, the shaft has a neck 37 that includes at least one flat surface. The bearing seat 44 includes a spheroidal body 45 with an upper spherical bearing surface 46, a base 47 with a lower friction surface 48, and a central passage 49 which is received about the shaft 43. The central passage 49 is keyed to a longitudinal groove 50 extending along a portion of the shaft length inhibiting rotation of the bearing seat 44 about the shaft while permitting longitudinal translation of the seat 44 up the shaft to the extent of the groove 50. The base 48 frictionally engages the upper surface 18 of the frame 8 when the carriage is loaded in the track 24 and the lower friction surface 48 may be roughened or include teeth, ridges, or other friction enhancing features.

Figure 11:
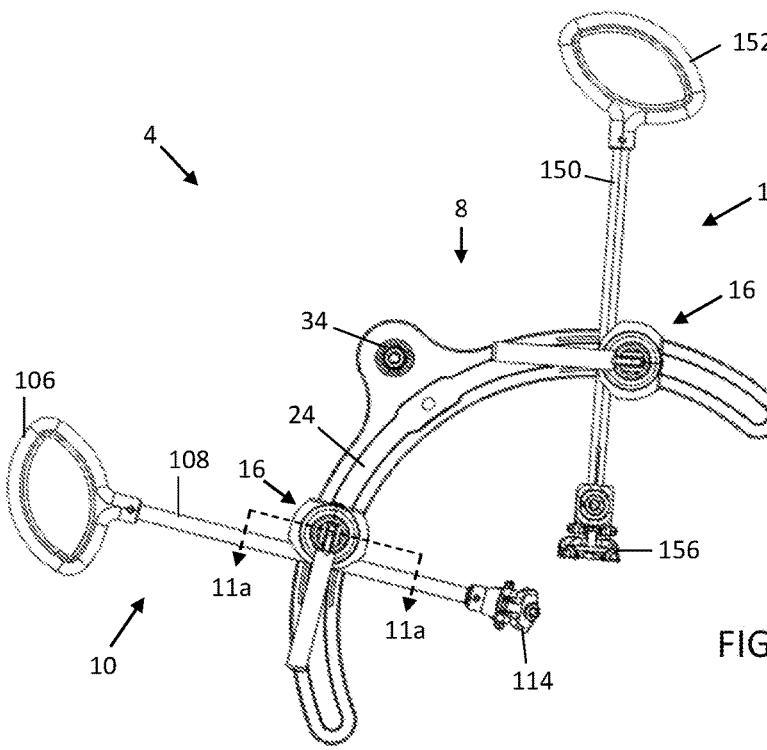
FIG. 11 is a top view of the main retractor assembly of FIG. 2 with a carriage coupled to the frame and a retractor blade assembly with the carriage in the locked position.
Figure 11A:
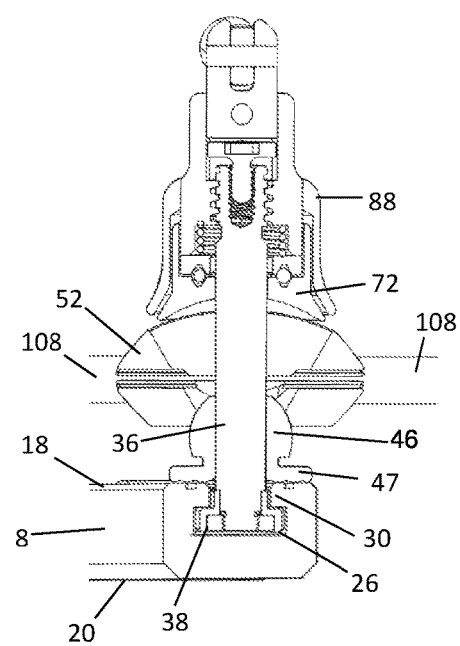
FIG. 11a is a cross section view of the main retractor assembly of FIG. 11.
Figure 12:
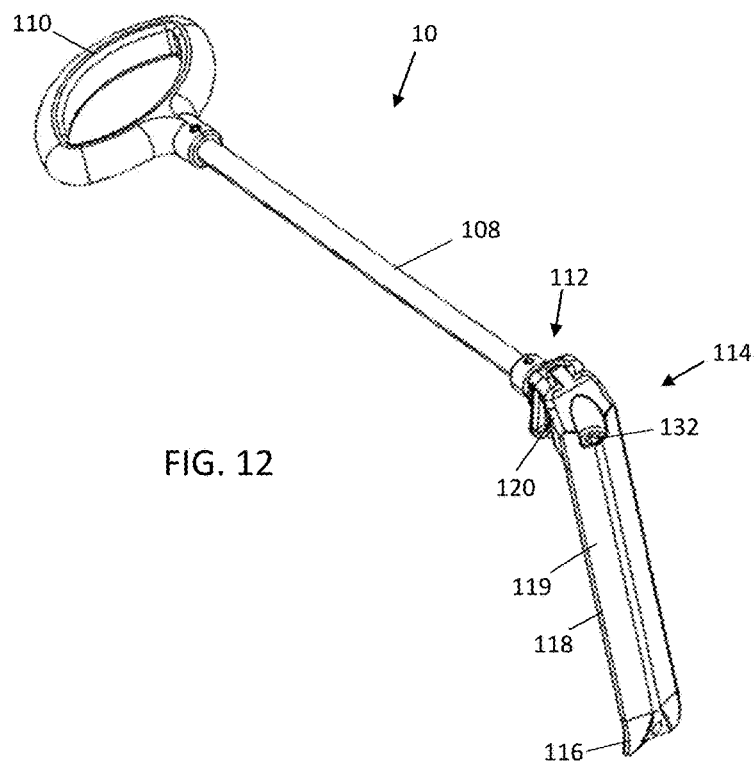
FIG. 12 is a perspective view of a first retractor blade assembly forming part of the retractor assembly of FIG. 1.
Figures 13, 14, 15:
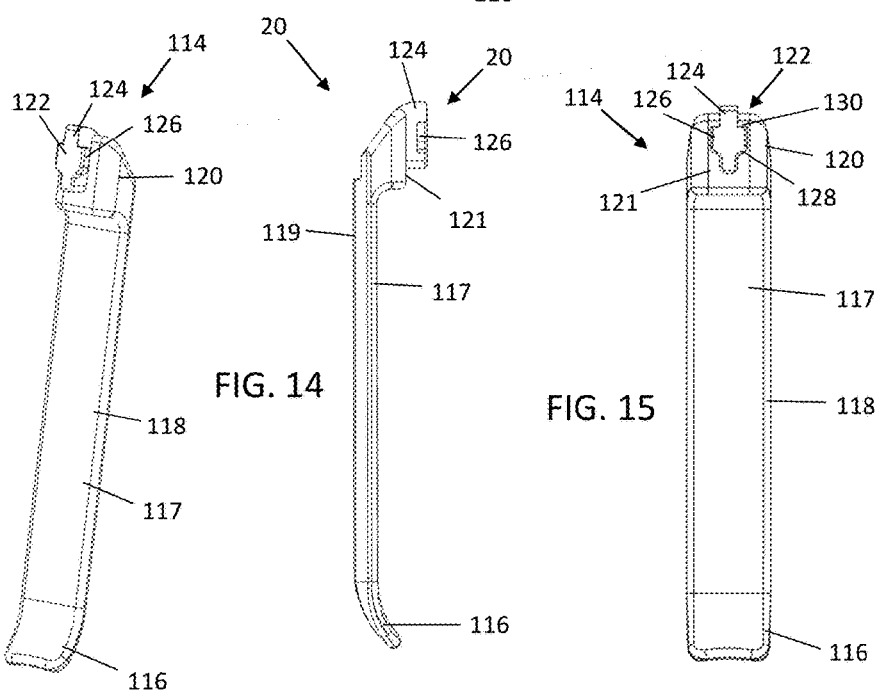
FIG. 13 is a rear perspective view of a retractor blade of the first retractor blade assembly of FIG. 12.
FIG. 14 is a side view of the retractor blade of FIG. 13.
FIG. 15 is a rear view of the retractor blade of FIG. 13.

The foot 38 is configured to engage the track 24 of frame 8. The maximum width and height of the foot 38 are configured such that the foot can be slidably received in the distal groove 26 of track 24 with the ledges 30 of the proximal neck 28 extending over the foot 38 such that the foot is vertically constrained in the track 24, as best viewed in FIG. 11a. The foot 38 is generally peanut shaped having a length greater than the width and a pair of bulbous ends curving into a narrower center. A pedestal 39 seated on top of foot slides through the neck when the foot is engaged in track 24. The track opening 32 is sized to allow the foot 38 to enter and engage the groove 26 underneath the neck 28. The peanut shape allows the foot to translate along the arced track 24 without binding while also preventing rotation of the foot 38 within the track 24. As such, the same side of the carriage 16 always faces the center of the circle defined by the frame 8. Assuming that the incision is approximately in the center of the circle defined by the frame, such a configuration has the advantage of keeping a retractor blades oriented toward the incision while the carriages 16 translate along the track 24.

Stacked atop the bearing seat 44, one on top of the other along the column 36, the carriage 16 further includes a blade holder 52, compression cap 72, and locking cap 88. The blade holder 52 is divided into an upper arm 54 and a lower arm 56 that are separated by a notch 58 that permits flex between the upper and lower arms, the notch opening on one side of the blade holder and extending to a sidewall 59 on the opposite side. The notch opening opposite the sidewall widens to a blade channel 60 dimensioned to receive a blade post of a retractor blade assembly. Tapered ends cause the upper and lower arms 54, 56 to flex apart as the blade post is pressed into the blade channel 60. Compression stops 62 situated adjacent the blade channel prevent over compression of the upper and lower arms. The under surface of the blade holder 52 has first bearing socket 66 that receives and mates with the bearing seat 44 spherical bearing surface 49 with the column shaft 43 passing through a central passage 64. The central passage 64 has an elliptic cone shape extending upward from the first bearing socket that allows the blade holder to rotate around the shaft 43 on the bearing seat 44. By way of example, the elliptic cone is dimensioned such that the blade holder can rotate 30° in the front to back direction (i.e. in line with blade channel 60) and 15° in the side to side direction. The upper surface 68 of the blade holder is spherical and may be roughed to increase locking friction with the compression cap 72.

The compression cap 72 has a spherical under surface 74 against which the upper surface of the compression cap 72 rotates. The lower surface 74 may also be roughened to increase locking friction with the upper surface 68 of the blade holder. A lower spring cavity 76 sits above the spherical under surface 74 and is bounded by an outer wall 78. Center passage 80 connects the lower spring cavity 76 and under surface 74 and includes at least one flat surface to engage with flat surface 37 of the column neck and prevent rotation of the compression cap around the column 36.

The locking cap 88 has an outer cup 90 fixed to a drive nut 92. By way of example, the cup is fixed to the drive nut by pins 94 that extend into apertures in the drive nut. A distal wall 95 of the drive nut 92 surrounds an upper spring cavity 98 and extends into the outer cup hollow defining a gap 96 between the outer cup 90 and the drive 92. The gap 96 is dimensioned to receive the compression cap outer wall 78 as the locking cap advances toward the compression cap to lock the carriage 16. A superior cavity 104 is situated in the locking nut 92 and is separated from the upper spring cavity by an internally threaded passage 100. The internal thread of passage 100 mates with the exterior thread of column head 40 to advance the locking cap up and down along the column 36 as the locking cap is rotated. A handle 106 is coupled to the locking nut 92 by a pivot such that it can be rotated out of the way if necessary once the carriage is locked. A set screw 102 threadedly engages the internal threading 42 on the column head to fix the carriage components together. The head of the set screw 102 resides in the superior cavity 104 to define the upper and lower limits of the lock nut travel relative to the column 16. A thrust bearing 82, bearing cap 84, and return spring 86 are housing in the upper and lower spring cavities to tension the compression cap 72 against the blade holder 52 when the carriage is unlocked.

In use, carriages 16 are coupled to the frame 8 while in the unlocked configuration. The foot 38 is advanced into the opening 32. An upward force is applied to the compression cap 72, compressing the return spring 86 and pushing the compression cap 72 up into the locking cap 86 with the outer wall 78 sliding into gap 96. This provides space for the blade holder 52 to rise proximally relative to the foot 38, which in turn provides space for the bearing seat 44 to rise proximally relative to the foot 38 such that the bearing seat base 47 clears the track neck 28, allowing the foot 30 to be advanced into the distal groove 26 of the track 24. The upward force may be applied to the compression cap 72 by holding the locking cap 88 and lifting up on the blade holder 52. Once the carriage 16 is advanced to the desired position along the track and the upward force is removed, the return spring 86 redirects the compression cap 72, blade holder 52, and bearing seat 44 downward such that the friction surface 48 of the base 47 works against the upper surface 18 of the track 24 to hold the carriage in place. With the carriages 16 coupled to the frame 8, the first and second blade assemblies 10, 12 are attached by side loading the blade posts 108, 150 into the respective blade channels 60 of the blade holder 52.

With the blade assemblies 10, 12 coupled to the blade holders 52, the retractor blades can be adjusted through 5 degrees of freedom relative to the frame 8 to precisely position the blades in the proper location and orientation. In the present example the 5 degrees of freedom are yaw, pitch, roll, surge, and sway, with yaw being rotation about the z-axis, pitch being rotation about the y-axis, roll being rotation about the x-axis, surge being translation along the x-axis, and sway being translation along the y-axis. Yaw, pitch, and roll are achieved via rotation of the blade holder 52 about the column as described above. Surge is achieved via translation of the blade post 108 through the blade channel 60 and sway is achieved via translation of the carriage 60 along the track 24. Additional roll may be achieved by rotation of the blade post 108 about its own longitudinal axis in the blade channel 60.

Once the blade assemblies 10, 12, coupled to the carriage and positioned as desired, the carriages 16 can be locked to inhibit further movement of the carriage and blade. To lock the carriage, the handle 106 is rotated to rotate the drive nut 92 and advance the internal threads distally along the column external threads. This advances the outer cup down along the compression cap until the outer wall is situated in the gaps, eliminating the space for the compression cap to move proximally. The compression cap presses the blade holder 52 and bearing seat distally. The blade holder is compressed between the compression cap and bearing seat and the friction between the components locks orientation of the blade holder. The upper and lower arms of the blade holder are also compressed around the blade post elimination the ability for the blade post to translate in the blade channel. The friction between the bearing seat base and the upper surface of the frame eliminates the ability for the carriage to translate along the track.

FIGS. 12-19a illustrate an example embodiment of the first blade assembly 10. The first blade assembly 10 includes a cylindrical blade post 10, a handle 110, blade connector 112 and first blade 114. The handle 114 provides a grip for manually holding, placing, and manipulating the first blade assembly 10. The post 108 has a diameter configured to be received in the blade channel 60 of the blade holder 52 and such that the blade post can be translated along its axis and/or rotated about its axis within the blade channel 60 until the upper and lower arms 54, 56 of the blade holder 52 squeeze against the post 108 when the carriage 16 is locked. Referencing FIGS. 12-15, the first blade 114 includes a distal end 116, an intermediate portion 118, and a proximal end 120. Between the proximal end and distal end on one side is a rear face 117 that is generally smooth and configured to engage body tissue surrounding the operative corridor. The distal end 116 is curved towards the rear and may have a slight concave end surface to lie against the curved surface of the vertebra and hold tissue back at the target site. An anchor channel 132 passes through the midline of the blade 114 adjacent the inner face 119. An anchor, such as a pin or screw (not shown) can be passed through the blade to secure the position of the blade relative to the spine and prevent blade shift should the patient or retractor be inadvertently jostled.

The proximal end of the blade 120 has an attachment feature 122 configured to engage and couple with the blade connector 112. The attachment feature 122 is in the form a vertical bar 124 extending rearward from a back wall 121 with a pair of narrow wings 126 extending horizontally along the midsection of the bar 124. The wings 126 do not have the same depth as the bar 124 such that there is a gap between each wing and the back wall 121. Each wing 126 has a tapered leading edge 128 of and a flat trailing edge 130.

Figure 16:
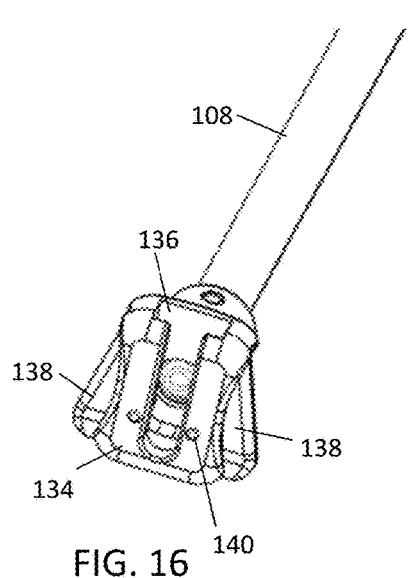
FIG. 16 is a perspective view depicting a blade connector forming part of the first retractor blade assembly of FIG. 12.
Figure 17:
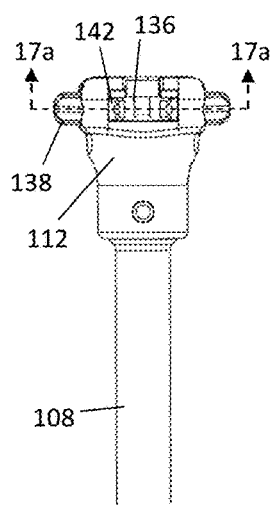
FIG. 17 is a top view of the blade connector of FIG. 16.
Figure 18:
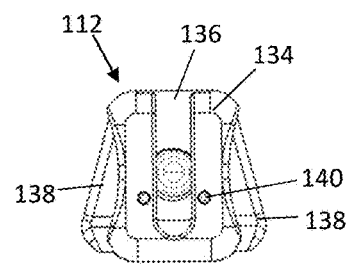
FIG. 18 is a front view of the blade connector of FIG. 16.
Figure 17A:
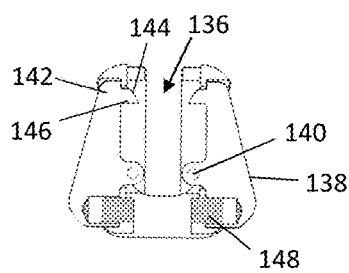
FIG. 17a is a cross-section view of the blade connector of FIG. 17.
Figure 19:
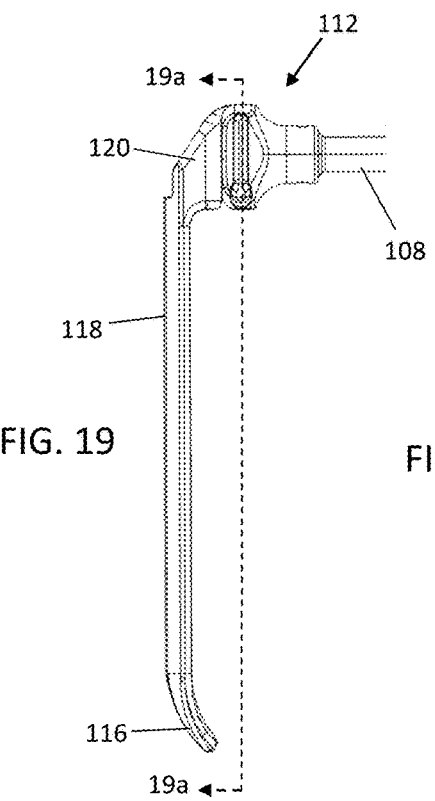
FIG. 19 is a side view of the distal end of the first blade assembly of FIG. 12 including the blade connector and attached blade.
Figure 19A:
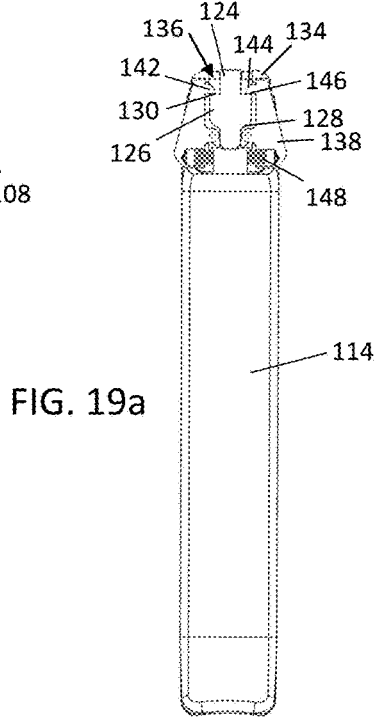
FIG. 19a is a cross-section view of the distal end of the first blade assembly of FIG. 19.

As shown in FIGS. 16-17a, the blade connector 112 is configured to receive attachment the feature 122 of blade 114 to rigidly couple the blade to the assembly 10. The connector includes a housing 134 that defines a receptacle 136 that will receive the attachment feature 122. The receptacle 136 is T-shaped with a rear slot dimensioned to receive the wings 126 and a narrow neck dimensioned to receive only the vertical bar 124 such that the wings 126 are captured within the slot. A pair of locking arms 138 are coupled to the housing 134 at a pivot 140. A locking head 142 of the locking arm 138 extends into the slot. The locking head has a tapered upper surface 144 and a flat lower surface 146. A spring 148 biases the locking arm in a locked position with the locking head extending into the receptacle slot. To couple the blade 114, the attachment feature is simply aligned with the receptacle and advanced. The tapered leading edges of wings 126 engaged the tapered upper surfaces 144 of the locking heads 142 causing the arms to swing outwards and allowing the wings to pass. Once the wings 126 pass the locking heads 142, the locking heads return to their biased locking position where the flat lower surfaces 146 engage the flat trailing surfaces of the wings 126 preventing their removal, as depicted in FIG. 19a. To remove the blade 114 the locking arms are depressed to swing the locking heads 142 out of the receptacle and the blade 114 is simply lifted out.

FIGS. 20-27a illustrate an example embodiment of the second blade assembly 12. The second blade assembly 12 includes a cylindrical blade post 150, a handle 152, blade connector 154 and second blade 156. The handle 152 provides a grip for manually holding, placing, and manipulating the second blade assembly 12. The post 150 has a diameter configured to be received in the blade channel 60 of the blade holder 52 and such that the blade post can be translated along its axis and/or rotated about its axis within the blade channel 60 until the upper and lower arms 54, 56 of the blade holder 52 squeeze against the post 150 when the carriage 16 is locked. Referencing FIGS. 20-23, the second blade 156 includes a distal end 158, an intermediate portion 160, and a proximal end 162. Between the proximal end and distal end on one side is a rear face 166 that is generally smooth and configured to engage body tissue surrounding the operative corridor. The distal end 158 is curved towards the rear and may have a slight concave end surface to lie against the curved surface of the vertebra and hold tissue back at the target site. A pair of anchor channels 164 pass through the second blade 156 adjacent the inner face 163. The anchor channels 164 are situated along the sides of the blade and may slightly converge in the distal direction to increase stability of the anchorage. Anchors, such as a pins or screws (not shown) can be passed through the anchor channels 164 to secure the position of the blade relative to the spine and prevent blade shift should the patient or retractor be inadvertently jostled. A center slot 165 on the inner face 163 may be included to interface with other tools that may be inserted into the access corridor, such as, for example, a light cable (not shown).

The proximal end of the blade 162 has an attachment feature 168 configured to engage and couple with the blade connector 154. The attachment feature 168 is in the form a vertical bar 170 extending rearward from a back wall 161 with a pair of narrow wings 172 extending horizontally along the midsection of the bar 170. The wings 172 do not have the same depth as the bar 170 such that there is a gap between each wing and the back wall 161. Each wing 172 has a tapered leading edge 174 of and a flat trailing edge 176.

As shown in FIGS. 16-17a, the blade connector 154 has an attachment housing 178 configured to receive attachment the feature 168 of the second blade 156 to rigidly couple the blade to the assembly 12. The blade connector 154 also includes a tilt housing 193 that may be operated to angulate the 156 blade relative to the post 150. The attachment housing 178 defines a receptacle 180 that will receive the attachment feature 168. The receptacle 180 is T-shaped with a rear slot dimensioned to receive the wings 172 and a narrow neck dimensioned to receive only the vertical bar 170 such that the wings 172 are captured within the slot. A pair of locking arms 182 are coupled to the housing 178 at a pivot 184. A locking head 186 of the locking arm 182 extends into the slot. The locking head has a tapered upper surface 188 and a flat lower surface 190. A spring 192 biases the locking arm in a locked position with the locking head extending into the receptacle slot. To couple the blade 156, the attachment feature 168 is simply aligned with the receptacle 180 and advanced. The tapered leading edges 174 of wings 172 engaged the tapered upper surfaces 188 of the locking heads 186 causing the arms to swing outwards and allowing the wings 172 to pass. Once the wings 172 pass the locking heads 186, the locking heads return to their biased locking position where the flat lower surfaces 190 engage the flat trailing surfaces 176 of the wings 172 preventing their removal, as depicted in FIG. 26a. To remove the blade 156 the locking arms are depressed to swing the locking heads 186 out of the receptacle and the blade 156 is simply lifted out.

Referring to FIGS. 25 and 26a, the tilt housing 193 sits behind the attachment housing 178 and couples to the post 154 such that the blade connector can angulate relative to the post 150. To do so the post 150 includes a pair of clamping arms 194 separated by a notch. The arms 194 end in circular clamping elements 196 separated by a space. An inner disc 200 extending from the back of the attachment housing 154 is situated between the clamping elements 196. Inner surfaces of the clamping elements and the outer surfaces of the inner disc 200 are ridged or scalloped to provide a secure and rigid connection when the blade angle is locked. An axel 198 passes through the a center hole in each of the clamping elements 196 and inner disc 200 to couple the arms to the connector 154 and provide a pivot about which the blade connector rotates. A rear opening 210 in the tilt housing 193 allows the blade to rotate through a full range of motion up to 90°. An upper opening houses a lock nut 202 that is coupled to the housing opening such that it rotates but does not translate relative to the housing. The locking nut 202 is threadedly coupled to a shaft 204 that passes through a threaded inner aperture in the locking nut. The shaft 204 is coupled to a locking press 206 with fingers 208 that fit around the clamping elements 193. The ends of the fingers 208 are tapered and complement tapered edges of the clamping elements 196. When the shaft 204 is fully raised into the locking nut 202 the locking press 206 allows the clamping elements rest in their open state such that the ridges on the clamping elements and inner disc 200 do not engage and the disc 200, along with the blade connector 154 and blade 156, can rotate relative to the clamping element 193 and post 150. When the locking nut 202 is rotated the shaft 204 is lowered into the housing and the locking press fingers 208 engage the sides of the clamping elements 196 squeezing them together to engage the ridges on the clamping elements 196 with those on the inner disc 200, locking the angular position of the blade.

In the present example, the first blade assembly 10 has been shown as a fixed blade and the second blade assembly 12 has been shown as an adjustable blade. However, it should be appreciated that position of the first blade assembly 10 and the second blade assembly 12 may be swapped on the retractor frame 8 from that shown herein. Alternatively, both the first retractor assembly and the second retractor assembly may use a fixed assembly like that shown in FIGS. 12-23, or, each of the first blade assembly and the second blade assembly may use an adjustable assembly like that shown in FIGS. 24-27*a*, depending on the patient's anatomy and the surgeon's needs or preferences. The adjustable assembly provides additional flexibility to the retractor while the rigid assembly provides a lower profile. Similarly, the narrow blade 114 depicted with first blade assembly 10 and the wider blade 156 depicted with second blade assembly 12 may also be swapped and used in any of the above combination as well.

Figure 34:
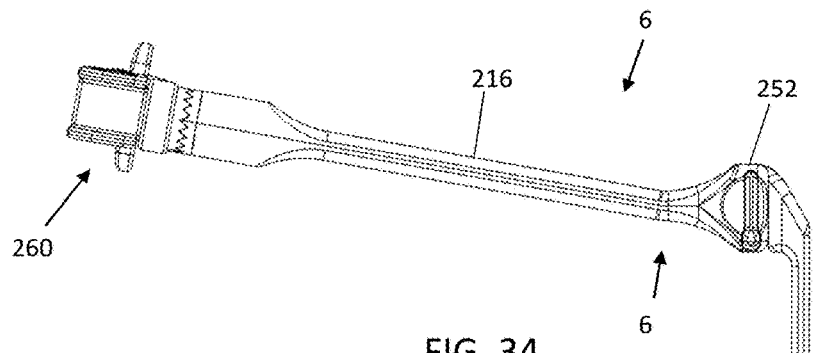
FIG. 34 is a side view of the third blade assembly of FIG. 28 forming part of the retractor assembly of FIG. 1.
Figure 35:
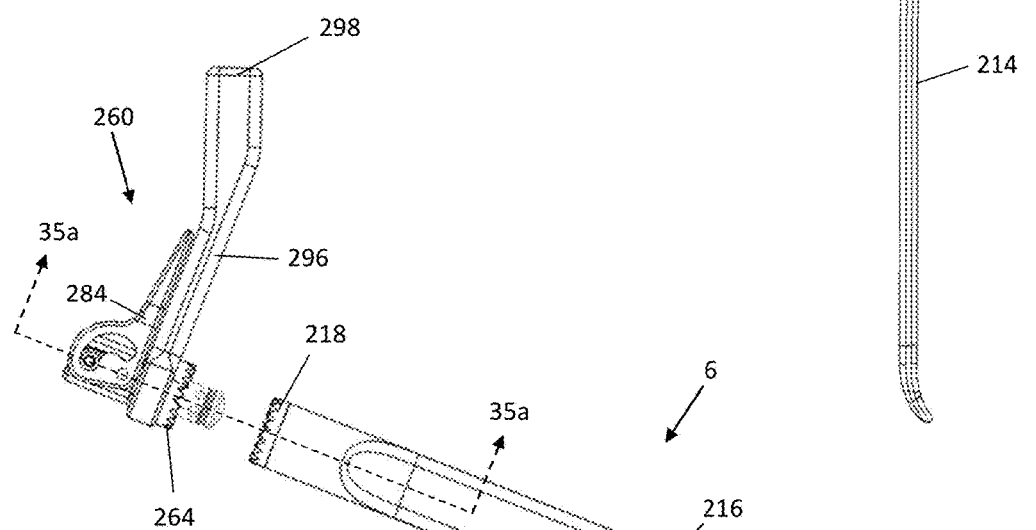
FIG. 35 is an exploded perspective view of the third blade assembly of FIG. 34 with a mount coupler separated from a connector of the blade assembly.
Figure 35A:
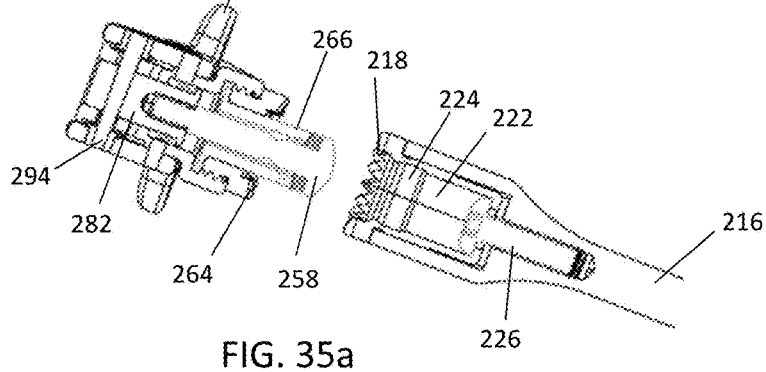
FIG. 35a is a cross-section view of a proximal end of the third blade assembly of FIG. 34.
Figures 36, 36A:
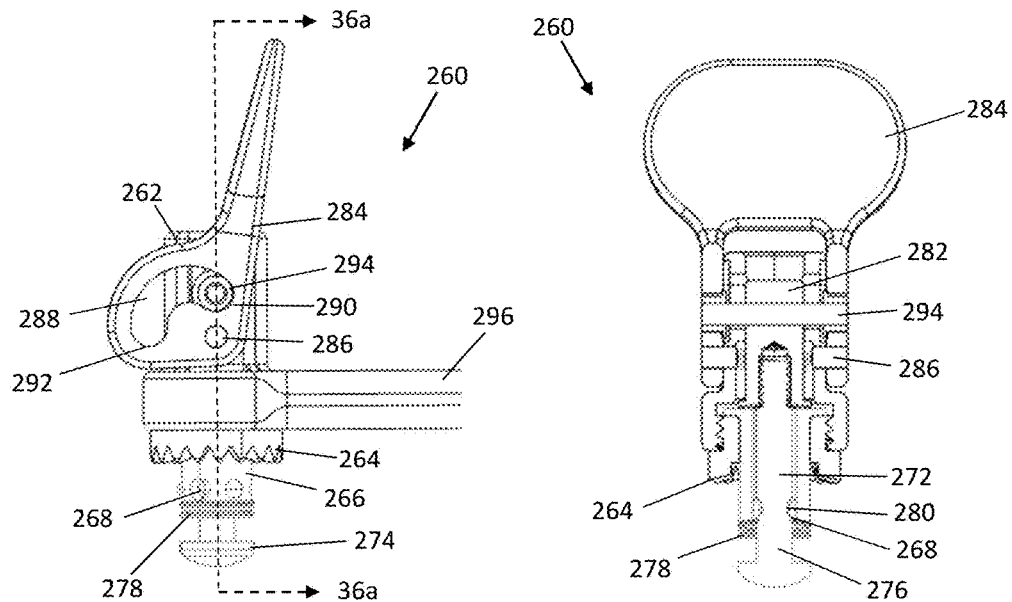
FIG. 36 is a side view of the coupler of FIG. 34 shown in an unlocked configuration.
FIG. 36a is a cross-section view of the coupler of FIG. 36.
Figures 37, 37A:
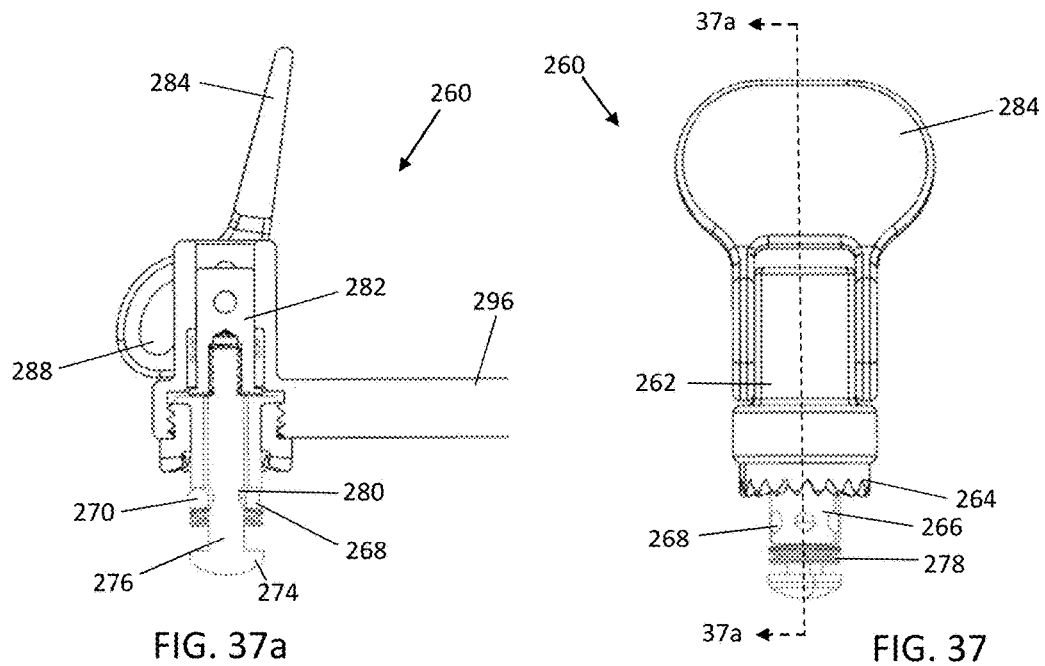
FIG. 37 is a front view of the coupler of FIG. 34 shown in an unlocked configuration.
FIG. 37a is a cross-section view of the coupler of FIG. 37.
Figure 38:
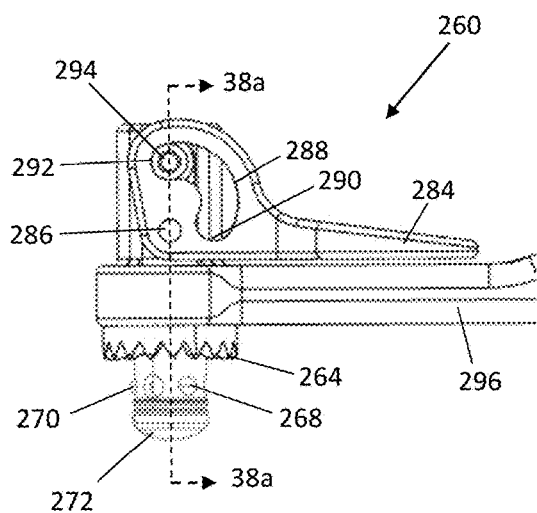
FIG. 38 is a side view of the coupler of FIG. 34 shown in a locked configuration.
Figure 38A:
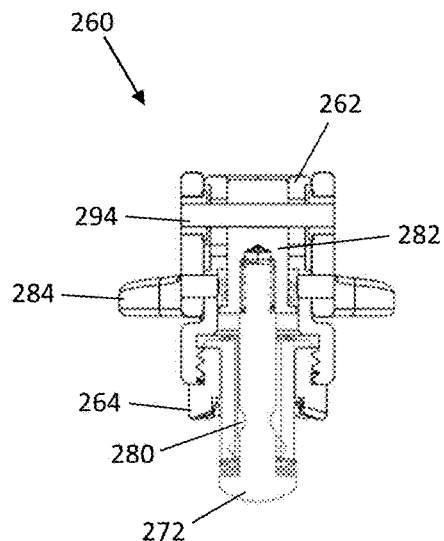
FIG. 38a is a cross-section view of the coupler of FIG. 38.
Figure 39A:
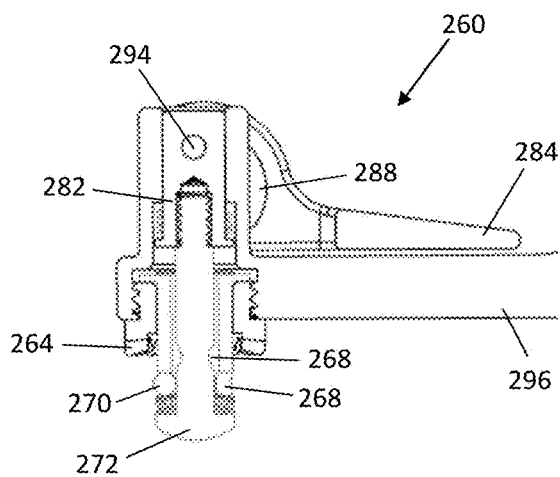
FIG. 39a is a cross-section view of the coupler of FIG. 39.
Figure 39:
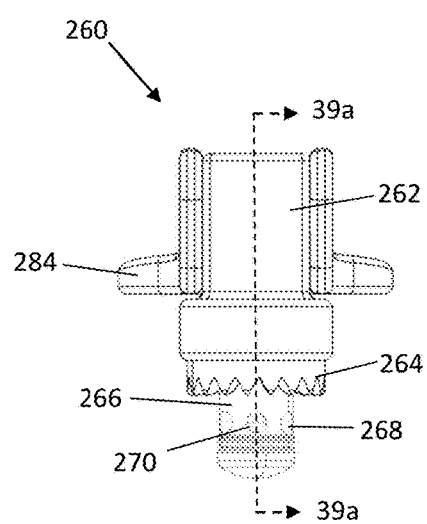
FIG. 39 is a front view of the coupler of FIG. 34 shown in a locked configuration.

FIGS. 28-34 illustrate, by way of example, the third blade assembly 14 and FIGS. 35-39*a* depict the coupler 260 that connects the third blade assembly to a rigid mount. The third blade assembly 14 includes blade extension 212 and third blade 214. The blade extension includes a shaft 216, mount connector 218, and blade connector 228. Referring to FIGS. 33-35, the mount connector 218 includes a "poker chip" face with ridges and a female receptacle. Within the receptacle 222 is a circumferential groove 224 and a screw 226 that attaches the connector to the shaft 216.

The third retractor blade is depicted, by way of example, in FIGS. 28-32. The third blade 214 includes a distal end 230, an intermediate portion 232, and a proximal end 234. Between the proximal end and distal end on one side is a rear face 240 that is generally smooth and configured to engage body tissue surrounding the operative corridor and on the opposite side is inner face 236. The distal end 230 is curved and the profile reduced on the rear face to create a saddle. The curve projects away from the rear such that it creates a forward hook at the distal end 230. This forward hooks scoops around the side of the vertebra and creates leverage to better hold the blade in position. A center slot 238 on the inner face 236 may be included to interface with other tools that may be inserted into the access corridor, such as, for example, a light cable (not shown). The proximal end of the blade 234 has an attachment feature 242 configured to engage and couple with the blade connector 228. The attachment feature 242 is in the form a vertical bar 244 extending rearward from a back wall 241 with a pair of narrow wings 246 extending horizontally along the midsection of the bar 244. The wings 246 do not have the same depth as the bar 244 such that there is a gap between each wing and the back wall 241. Each wing 246 has a tapered leading edge 248 of and a flat trailing edge 250.

The attachment housing 252 defines a receptacle 254 that will receive the attachment feature 242. The receptacle 254 is T-shaped with a rear slot dimensioned to receive the wings 246 and a narrow neck dimensioned to receive only the vertical bar 244 such that the wings 246 are captured within the slot. A pair of locking arms 256 are coupled to the housing 252 at a pivot 258. A locking head (not shown) of the locking arm 252 extends into the slot. The locking head has a tapered upper surface and a flat lower surface and is spring biased to a locked position with the locking head extending into the receptacle slot. To couple the blade 214, the attachment feature 242 is simply aligned with the receptacle 254 and advanced. The tapered leading edges of wings 248 engaged the tapered upper surfaces of the locking heads causing the arms to swing outwards and allowing the wings 246 to pass. Once the wings 246 pass the locking heads, the locking heads return to their biased locking position where the flat lower surfaces engage the flat trailing surfaces 250 of the wings 246 preventing their removal. To remove the blade 214 the locking arms are depressed to swing the locking heads out of the receptacle and the blade 214 is simply lifted out. The attachment housing is set at an angle relative to the shaft 116 such that the angle between the third blade 214 and the shaft 216 is greater than 90°. By way of example, the angle of the housing is set such that the blade angle is 100°. This angle provides extra clearance for the surgeon to get a hand between the patient and the shaft in order to manipulate the blade assembly 14 better.

The coupler 260 engages the mount connector 218 is rigidly attached to a rigid mount, such as, an articulating arm table mount or A-arm (not shown) at one end and attaches to the mount connector 218 of the third blade assembly 14 at the other end. The mount 260 has a housing 262 with a "poker chip" face 264 on one end that complements and engages the "poker chip" face of the mount connector 218. A hollow cylinder 266 extends through the face 264 and includes a series of circular apertures 268 arrayed around and end of the cylinder and one or more balls 270 aligned with the apertures. A plunger 272 extends through the cylinder 266 and is coupled to piston 282. The distal end 274 of the plunger has an enlarged head that sits beyond the end of the cylinder 266 and is separated from the cylinder by a series of bellville washers 278 that provide a spring force to the plunger. The shaft 276 of the plunger 272 includes detents 280 that align with the balls 270 when the coupler is in the unlocked position. This allows the balls 270 to retreat into the apertures 268. In the locked position the shaft 276 forces the balls 270 to partially extend out of the apertures 268. To move the coupler between the locked and unlocked positions, the plunger is connector to the piston 282 which is coupled to a lever 284. The lever connects to the housing 262 at a pivot point via pivot pins 286. Above the pivot pins the housing includes a translation slot that houses a translation bar 294 that slides up and down the slot. Ends of the translation bar 294 are situated in arcuate tracks 288 on the sides of the lever. A first end 290 of the arcuate track is situated closer to the pivot point than a second end 292 such that as the lever rotates around the pivot, the translation bar 294 moves up or down moving the piston along with it. To couple the third blade assembly 14 to the coupler 260, the plunger 272 and cylinder 266 are inserted into the female receptacle 222 on the mount connector 218 with the lever in the unlocked position such that the plunger 271 is extended. The lever 284 is rotated to the locked position drawing the plunger 272 into the cylinder 266 allowing the "poker chip" faces to engage and forcing the balls 270 through the apertures where they engage with the circumferential groove 224 to lock the coupler 260 and connector 218 together. A rigid extension arm 296 of the coupler extends away from the housing 262 and includes an adapter, which may be threading or other suitable feature, which connects the coupler to the table mount (not shown).

Figure 40:
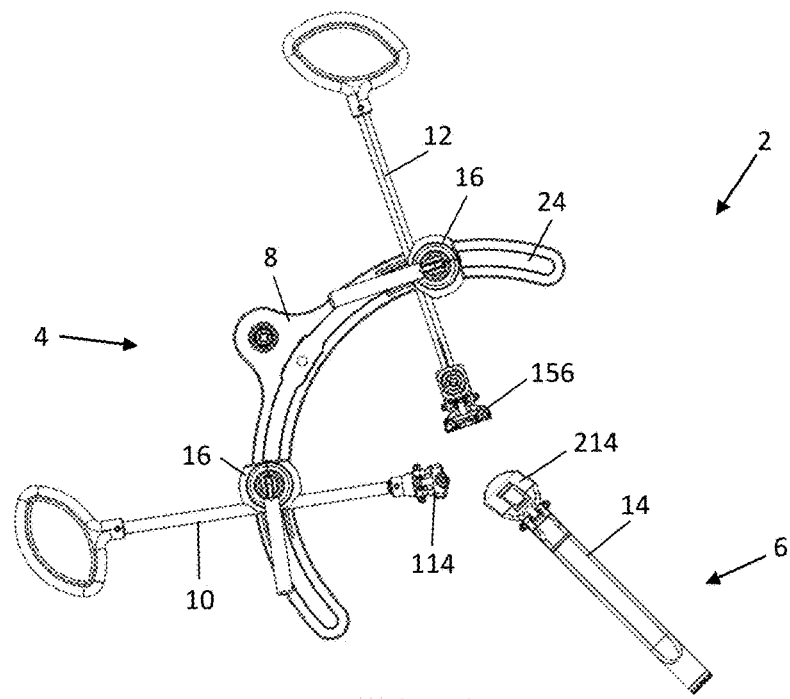
FIG. 40 is a top view of the retractor assembly of FIG. 1.
Figure 41:
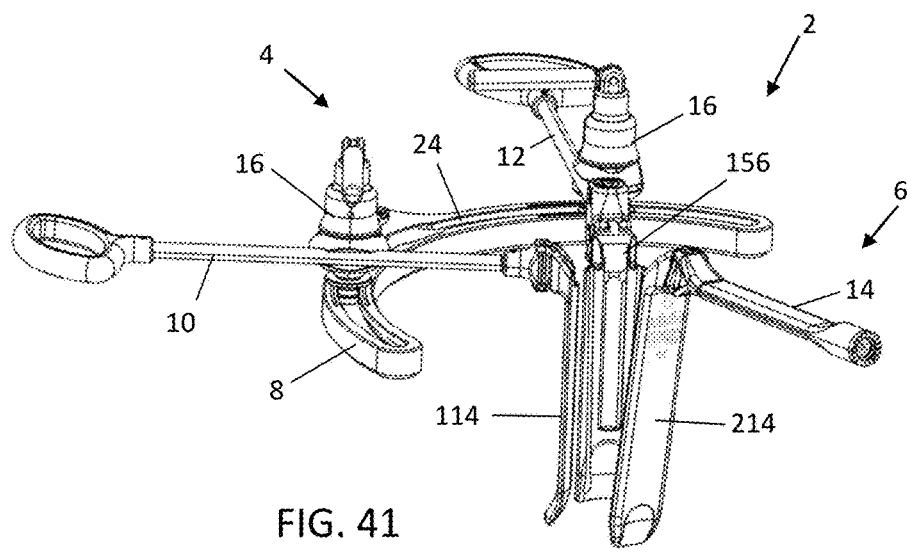
FIG. 41 is a perspective view of the retractor assembly of FIG. 1.

In use, the retractor assembly 2 is deployed to create and maintain an access or operative corridor to the spine of a patient. By way of example, the retractor assembly 2, as configured and described above is particularly well suited for creating an access corridor to the spine from an anterior approach (e.g. ALIF), and even more particularly an anterior approach performed with the patient situated in the lateral decubitus position (e.g. Lateral ALIF). For example, as illustrated in FIGS. 40-41, a final configuration for performing a Lateral ALIF may include just three retractor blades, rather than the four or more retractor blades typically used for an ALIF approach. This reduction in blade count helps facilitate imaging of the surgical site (e.g. via fluoroscopy) and manipulation of instrumentation through the operative corridor because there is less material around the access corridor to provide obstruction. Likewise, utilizing and independently fixed third blade assembly, rather than coupling the third blade to the frame reduces the frame length needed, further reducing the material around the access corridor that can obstruct imaging and or instrument manipulation. For example, unlike normal anterior retractor frames, the frame extends around less than half of the perimeter. The independent third blade is also useful in better facilitating the positioning of the third blade 214 in a different plane than the first and second blades 114, 156, allowing the blade to more easily reach deeper along the medial side of the vertebra.

Figure 42:
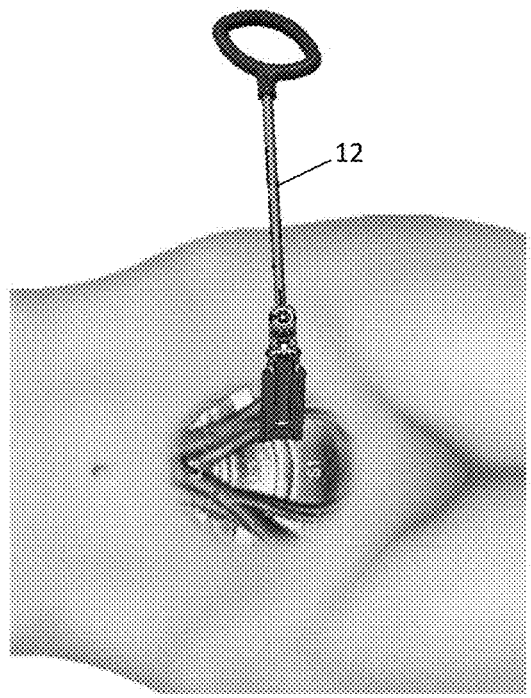
FIGS. 42-45 are illustrative images depicting example steps according to one exemplary method of utilizing the retractor assembly of FIG. 1 to perform a Lateral ALIF procedure at the L5-S1 disc of the lumbar spine.
Figure 43:
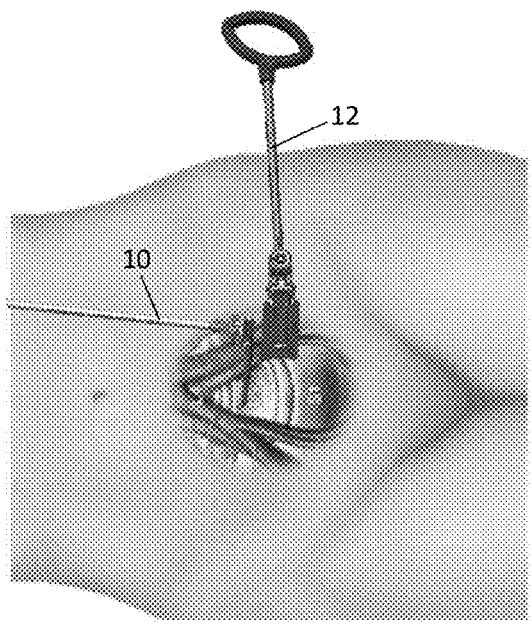
Figure 44:
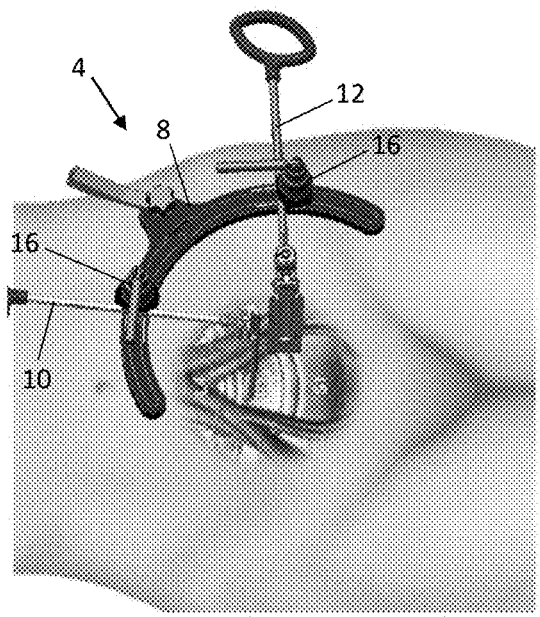
Figure 45:
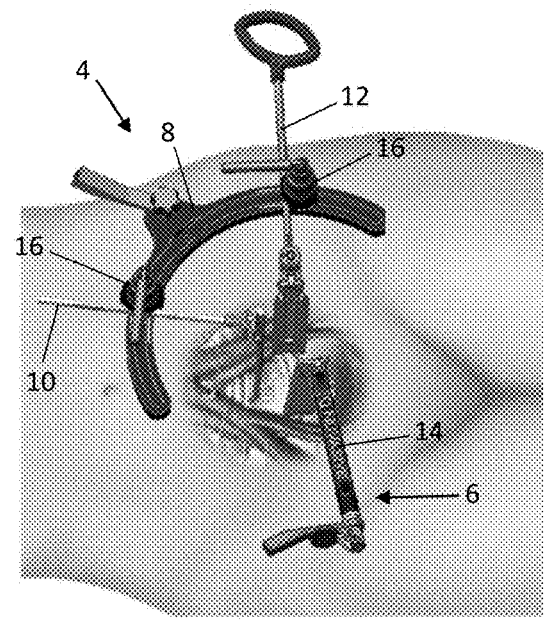

One example technique for performing a Lateral ALIF procedure to the L5-S1 disc space with the retractor assembly 2 is described hereafter by way of example. As noted, the patient is positioned on the table in the lateral decubitus position and appropriately secured using tape or other suitable tools. Following standard surgical preparation, the disc space is localized using lateral fluoroscopy. A template is used to make skin markings to define the iliac crest, inferior endplate of L5, superior endplate of S1, and midline. An oblique incision is made lateral to the rectus and cephalad to the inguinal ligament and an alternating blunt scissor and finger dissection is used to enter the retroperitoneal space. Once the index finger is inside the space, a gentle sweeping motion is used to palpate the left common iliac vessels and create a space through which second retractor blade 156 of the second blade assembly 12 may pass. Once a pathway to the disc space is created, the first (lateral) blade 156 is advanced through the retroperitoneal space and positioned medial to the descending common iliac vessels and lateral to the L5-S1 disc space with the distal end docked on the disc. (FIG. 42). Prior to advancing the retractor blade, a light cable (not shown) may be engaged in the slot 165, or otherwise directed into the incision. The distal end of the blade 156 may then be anchored with the placement a bone anchor through one of the anchor channels 164 and into the S1 vertebral body. Next, the first (cranial) retractor blade 114 may be guided down to the superior aspect of the disc space and below the descending vessel bifurcation (FIG. 43). The distal end of the blade may be anchored with the placement of a bone anchor through the anchor channel 132 into the L5 body. The frame 8 may be assembled with a pair of carriages 16 advanced into the track 24 and moved to align with the carriage markers 33, leaving the carriages in the unlocked configuration. The frame 8 is then centered around the incision with the lateral carriage marker oriented laterally and the cranial carriage marker 33 oriented cranially. A rigid table mount, for example, an A-arm mount (not shown) may then be coupled to the mount connect 34 to fix the position of the frame. The first and second retractor assemblies 10, 12, may then be coupled to the frame by snapping the posts 108, 150 into the blade channel 60 of the blade holder 52 (FIG. 43). The position and orientation of the carriage/blade holder may be adjusted in any of the 5° of freedom described above in order to engage the post with the blade holder. Once the blades 114, 156 are coupled to the blade holder 52, the handle 106 may be turned to advance the locking cap 88 and lock each of the carriages 16 as described above. With the main retractor 4 in place, the offset or independent retractor 6 with is placed in the medial position. The third (medial) blade 214 may be advanced through the incision and positioned over the L5-S1 disc space. Because the patient is in the lateral decubitus position the abdominal contents tend to fall away and the third blade 114 functions more to form a barrier and maintain tissue out of the corridor than to actually fully retract tissue. This both allows the third blade 214 to function effectively without a fourth blade as is with other ALIF retractors and procedures and facilitates advancement of the third blade 214 farther down along the side of the vertebral body where the forward hook of the distal end 230 hook around the vertebrae and leverage against it to maintain good position as the blade 214 is angled down to increase the exposure. The third blade assembly is then rigidly fixed in position by attaching to a rigid table mount, by way of example, an A-arm table mount via the coupler 260. Once access to the disc space is achieved has been achieved, the surgeon may proceed with disc space preparation and implant placement.

Figure 46:
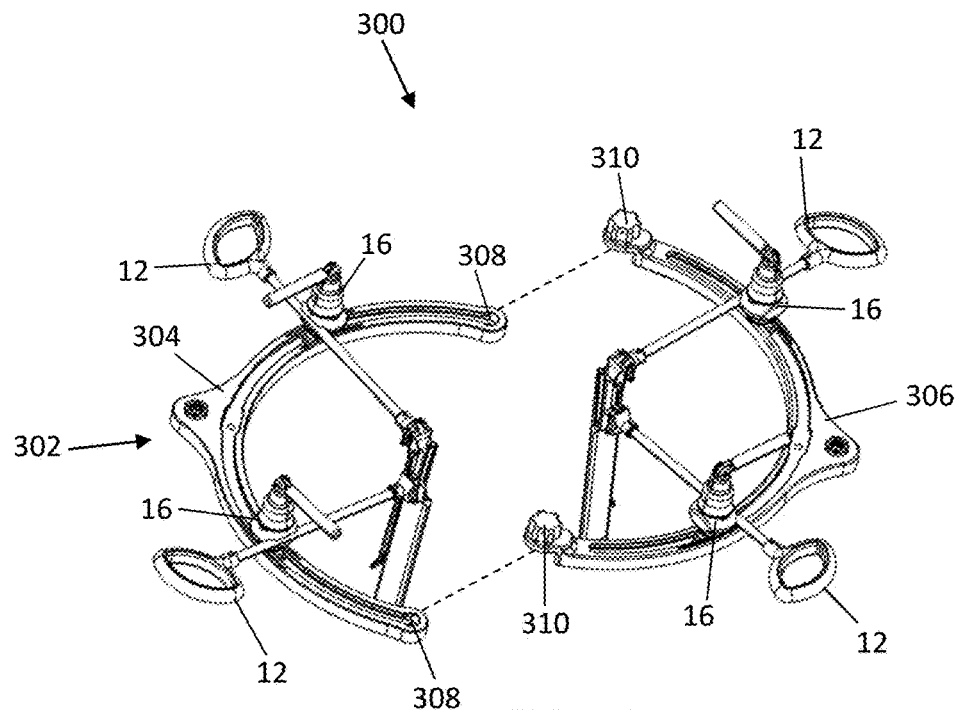
FIG. 46 is an exploded perspective view of a retractor assembly according to a second example embodiment configured for use in an anterior access surgery with the patient in the supine position, according to one example embodiment.
Figure 47:
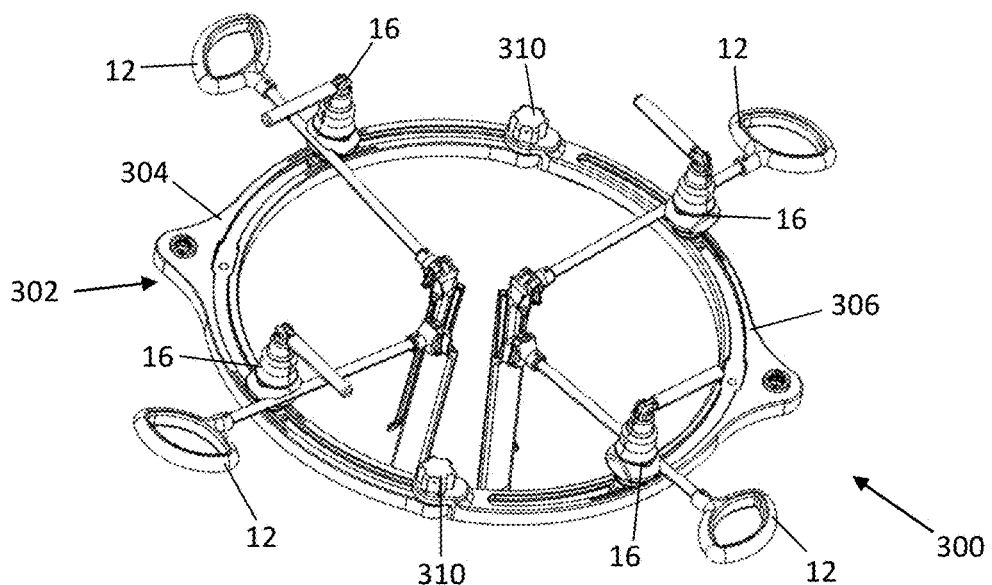
FIG. 47 is a perspective view of the retractor assembly of FIG. 46.

With reference to FIGS. 46-47 there is depicted an alternate configuration of a retractor assembly 300. The retractor assembly 300 is similar to the retractor assembly 2 in most respects, but is configured for use during standard or supine anterior access surgery. For example, the retractor assembly 30 utilizes four retractor blades rather than three. As shown, four second blade assemblies 12 are utilized and coupled to four carriages 16 respectively. It should be appreciated however that all four second blade assemblies 12 could be replaced with four first blade assemblies 10, or any combination of first blade assemblies 10 and second blade assemblies 12 could be used. Rather than a single piece, the frame 302 includes a first frame portion 304 and a second frame portion 306. Each frame portion is approximately 180° such that together they form a circle. The radius of the circle in the example show is approximately 12" which provides enough room that multiple levels may be performed without moving the retractor frame. The frame portions 304 and 306 are identical to the frame 8 previously described except for the radius and arc length as noted, and the first frame portion 304 includes two end openings 308 at the end of the track, and the second frame portion 306 includes two connectors 310 that engage in the openings to couple the first frame portion 302 and second frame portion 304 together.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. It is to be understood that any given elements of the disclosed embodiments of the invention may be embodied in a single structure, a single step, a single substance, or the like. Similarly, a given element of the disclosed embodiment may be embodied in multiple structures, steps, substances, or the like. The embodiments described hereinabove are further intended to explain certain best modes known of practicing the devices, instruments, techniques, and other teachings of the present disclosure and to enable others skilled in the art to utilize the teachings of the present disclosure in such, or other, embodiments and with the various modifications required by the particular applications or uses. Accordingly, the devices, instruments, techniques, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A retractor assembly for forming an operative corridor to a spinal target site, the retractor assembly comprising:
    a main retractor assembly comprising a frame, a first mobile carriage comprising a first blade channel in a side of the first mobile carriage, a second mobile carriage comprising a second blade channel in a side of the second mobile carriage, a first retractor blade assembly, and a second retractor blade assembly, wherein the first retractor blade assembly is removably coupled to the first mobile carriage via the first blade channel, the second retractor blade assembly is removably coupled to the second mobile carriage via the second blade channel, and wherein the first and second mobile carriages are coupled to the frame, wherein the first retractor blade assembly comprises a first retractor cylindrical body having a first retractor cylindrical body distal end and a first retractor cylindrical body proximal end, the first retractor cylindrical body further comprising a first retractor cylindrical body diameter, the first retractor blade assembly further comprising a first retractor handle configured to be grasped by hands of a human user, the first retractor handle secured to the first retractor cylindrical body proximal end and comprising a first retractor handle width, wherein the first retractor handle width is larger than the first retractor cylindrical body diameter, wherein the first blade channel is configured to receive the first retractor cylindrical body via side-loading through the side of the first mobile carriage, and wherein the second retractor blade assembly comprises a second retractor cylindrical body having a second retractor cylindrical body distal end and a second retractor cylindrical body proximal end, the second retractor cylindrical body further comprising a second retractor cylindrical body diameter, the second retractor blade assembly further comprising a second retractor handle configured to be grasped by hands of a human user, the second retractor handle secured to the second retractor cylindrical body proximal end and comprising a second retractor handle width, wherein the second retractor handle width is larger than the second retractor cylindrical body diameter, wherein the second blade channel is configured to receive the second retractor cylindrical body via side-loading through the side of the second mobile carriage; and
    an independent retractor assembly having a third retractor blade assembly that is directly coupleable to a rigid mount.

2. The retractor assembly of claim 1, wherein the frame includes a track, and the first mobile carriage and the second mobile carriage translate along the track.

3. The retractor assembly of claim 2, wherein the track includes a lower groove and an upper neck narrower than the lower groove.

4. The retractor assembly of claim 3, wherein the first and second mobile carriages each include a foot dimensioned to slide along the lower groove underneath the upper neck.

5. The retractor assembly of claim 4, wherein the first mobile carriage and the second mobile carriage each have a locked configuration in which translation along the track is inhibited and in which movement of the respective retractor cylindrical body within the respective blade channel is prevented.

6. The retractor assembly of claim 5, wherein each of the first mobile carriage and second mobile carriage include an unlocked configuration in which the coupled blade assembly is adjustable with five degrees of freedom.

7. The retractor assembly of claim 5, wherein the first and second carriages each include a column extending upwards from the foot and a bearing seat, blade holder, compression cap, and locking cap stacked atop one another along the column.

8. The retractor assembly of claim 7, wherein the bearing seat has a spherical bearing surface and the blade holder has a spherical bearing socket that bears on the spherical bearing surface.

9. The retractor assembly of claim 8, wherein the upper surface of the blade holder is a spherical surface and the compression cap has a spherical under surface that bears on the upper surface of the blade holder.

10. The retractor assembly of claim 9, wherein the blade holder rotates about the spherical bearing surface of the bearing seat and wherein the rotational freedom of the blade holder defines an elliptic cone.

11. The retractor assembly of claim 5, wherein each mobile carriage includes a lever at a top of the mobile carriage, wherein the lever is configured to pivot with respect to the respective mobile carriage from a substantially upright position to a substantially horizontal position, wherein pivotal movement of the lever between the substantially upright position to the substantially horizontal position transitions the respective mobile carriage between the unlocked configuration and the locked configuration.

12. The retractor assembly of claim 11, wherein one of the first and second blade assemblies is a fixed assembly wherein the angle of the retractor blade is fixed relative to the cylindrical body.

13. The retractor assembly of claim 11, wherein one of the first and second blade assemblies is an adjustable assembly wherein the angle of the retractor blade relative to the cylindrical body is adjustable.

14. The retractor assembly of claim 3, wherein the frame is arcuate and the track is arcuate extending from a first end to a second end along the arcuate frame.

15. The retractor assembly of claim 14, wherein the arcuate frame extends along an arc length of 150°.

16. The retractor assembly of claim 15, wherein the arc radius is 9 inches.

17. The retractor assembly of claim 15, wherein the frame is made of carbon fiber.

18. The retractor assembly of claim 15, wherein the frame includes a connector site that is coupleable to a rigid mount.

19. The retractor assembly of claim 14, wherein the track includes an opening lacking the upper neck wherein the first and second carriage foots are inserted into the lower groove.

20. A system for creating an anterior access corridor to a lumber spine with the patient in the lateral decubitus position, comprising:
a three bladed retractor assembly, wherein a first and a second of the three retractor blades are releasably coupled to an arcuate frame having an arc length of 180° or less and the third retractor blade is independent from the arcuate frame and is directly coupled to a rigid table mount to hold the third retractor blade in position, wherein each of the first and second retractor blades are secured to the arcuate frame via a rigid cylindrical blade post releasably secured to a track in a top surface of the arcuate frame, wherein each rigid cylindrical blade post comprises a distal end to which the respective retractor blade is secured and a proximal end to which a handle is secured, wherein the handle has a handle width greater than a diameter of the rigid cylindrical blade post, and wherein the handle is configured to be grasped by a human user in order to retract and advance the blade perpendicular to the track.

21. The system of claim 20, wherein the rigid cylindrical blade posts of the first and second retractor blades coupled to the arcuate frame are each coupled to the frame by a carriage, wherein each carriage comprises a blade channel having a channel side opening configured to receive a respective rigid cylindrical blade post via side-loading therethrough.

22. The system of claim 21, wherein each carriage includes an unlocked position in which the associated retractor blade is adjustable with five degrees of freedom relative to the frame.

23. The system of claim 22, wherein the carriages are movable along the track of the frame in the unlocked position.

24. The system of claim 23, wherein each carriage includes a locked position in which movement along the track is arrested.

25. The system of claim 23, wherein the locked position inhibits all movement of the associated retractor blade relative to the frame.

* * * * *